US012778922B1

(12) United States Patent
Trollsas et al.

(10) Patent No.: US 12,778,922 B1
(45) Date of Patent: Nov. 3, 2026

(54) TREATING BENIGN PROSTATIC HYPERPLASIA

(71) Applicant: RESURGE THERAPEUTICS, INC., San Jose, CA (US)

(72) Inventors: Olof Mikael Trollsas, San Jose, CA (US); John J. Stankus, Santa Cruz, CA (US); Shahram Shawn Gholami, Monte Sereno, CA (US)

(73) Assignee: RESURGE THERAPEUTICS, INC, San Jose, CA (US)

( * ) Notice: Subject to any disclaimer, the term of this patent is extended or adjusted under 35 U.S.C. 154(b) by 0 days.

(21) Appl. No.: 19/377,994

(22) Filed: Nov. 3, 2025

(51) Int. Cl.
*A61K 31/337* (2006.01)
*A61K 9/00* (2006.01)
*A61K 31/436* (2006.01)
*A61P 13/08* (2006.01)

(52) U.S. Cl.
CPC .......... *A61K 31/337* (2013.01); *A61K 9/0019* (2013.01); *A61K 31/436* (2013.01); *A61P 13/08* (2018.01)

(58) Field of Classification Search
None
See application file for complete search history.

(56) References Cited

U.S. PATENT DOCUMENTS

| | | | |
|---|---|---|---|
| 5,116,615 | A | 5/1992 | Gokcen et al. |
| 5,595,985 | A | 1/1997 | Labrie |
| 5,945,115 | A | 8/1999 | Dunn et al. |
| 6,177,404 | B1 | 1/2001 | DeFeo-Jones et al. |
| 6,277,391 | B1 | 8/2001 | Seo et al. |
| 6,689,803 | B2 | 2/2004 | Hunter |
| 6,759,431 | B2 | 7/2004 | Hunter |
| 7,008,633 | B2 | 3/2006 | Yang et al. |
| 7,015,253 | B2 | 3/2006 | Escandon et al. |
| 7,906,136 | B2 | 3/2011 | Wong et al. |
| 8,002,745 | B2 | 8/2011 | Kaal et al. |
| 8,133,491 | B1 | 3/2012 | Selman et al. |
| 8,313,763 | B2 | 11/2012 | Margaron et al. |
| 8,362,086 | B2 | 1/2013 | Soll et al. |
| 8,900,252 | B2 | 12/2014 | Lamson et al. |
| 9,186,464 | B2 | 11/2015 | Franklin |
| 9,545,464 | B2 | 1/2017 | Roche et al. |
| 9,814,685 | B2 | 11/2017 | Baltezor et al. |
| 10,004,813 | B2 | 6/2018 | Hochberg et al. |
| 10,159,683 | B2 | 12/2018 | Wong et al. |
| 10,265,477 | B2 | 4/2019 | Schwab et al. |
| 10,639,273 | B2 | 5/2020 | Puri et al. |
| 10,668,188 | B2 | 6/2020 | Wang |
| 10,792,427 | B2 | 10/2020 | Metzner et al. |
| 11,013,731 | B2 | 5/2021 | Kundu et al. |
| 11,097,061 | B2 | 8/2021 | Gerlett |
| 11,110,067 | B2 | 9/2021 | Sharp et al. |
| 11,602,516 | B1 | 3/2023 | Trollsas et al. |
| 11,911,499 | B2 | 2/2024 | Trollsas et al. |
| 11,957,654 | B2 | 4/2024 | Trollsas et al. |
| 11,974,979 | B2 | 5/2024 | Trollsas et al. |
| 12,090,136 | B2 | 9/2024 | Trollsas et al. |
| 2002/0055666 | A1 | 5/2002 | Hunter et al. |
| 2004/0002647 | A1 | 1/2004 | Desai |
| 2005/0064045 | A1 | 3/2005 | Zhong et al. |
| 2006/0063732 | A1 | 3/2006 | Vogel et al. |
| 2006/0217680 | A1 | 9/2006 | Barath |
| 2007/0042046 | A1 | 2/2007 | Saffie et al. |
| 2007/0280992 | A1 | 12/2007 | Margaron et al. |
| 2008/0194663 | A1 | 8/2008 | Dunn |
| 2008/0286205 | A1 | 11/2008 | Lennernas et al. |
| 2008/0317736 | A1 | 12/2008 | Franano |
| 2009/0227633 | A1 | 9/2009 | Damaj |
| 2009/0248034 | A1 | 10/2009 | Dolan et al. |
| 2010/0081681 | A1 | 4/2010 | Blagosklonny |
| 2013/0197446 | A1 | 8/2013 | Gustafsson et al. |
| 2013/0325143 | A1 | 12/2013 | Lamson et al. |
| 2014/0350516 | A1 | 11/2014 | Schwab et al. |
| 2015/0094667 | A1 | 4/2015 | Verhoeven et al. |
| 2015/0273117 | A1 | 10/2015 | Wang |
| 2015/0322064 | A1 | 11/2015 | Ren et al. |
| 2016/0024099 | A1 | 1/2016 | Ren et al. |
| 2020/0101012 | A1 | 4/2020 | Klein et al. |
| 2020/0113820 | A1 | 4/2020 | Pui et al. |
| 2020/0170992 | A1 | 6/2020 | Dizerega et al. |
| 2022/0031606 | A1 | 2/2022 | Trollsas et al. |
| 2022/0387731 | A1 | 12/2022 | Diaz et al. |
| 2023/0240979 | A1 | 8/2023 | Trollsas et al. |

(Continued)

FOREIGN PATENT DOCUMENTS

| | | | |
|---|---|---|---|
| CN | 100431631 | C | 11/2008 |
| EP | 1845942 | B1 | 4/2014 |

(Continued)

OTHER PUBLICATIONS

Hsu, Yu-Chao, Hung-Jen Wang, and Yao-Chi Chuang. "Intraprostatic botulinum neurotoxin type A injection for benign prostatic hyperplasia—a spotlight in reality." Toxins 8.5 (2016): 126.*
Ahmed, "Approaches to develop PGLA based in situ gelling system with low initial burst", Pak. J. Pharm. Sci., Mar. 2015, vol. 28, No. 2, pp. 657-665.
Belz, Jodi Elizabeth, "Smart brachytherapy spacers for combined chemo-radiation therapy: local delivery of nanoparticles, chemotherapeutics, and molecular inhibitors for cancer treatment", Diss. Northeastern University Boston, May 2017, 188 pages.
Bode et al., "Paclitaxel encapsulated in cationiciposomes: a new option for neovascular targeting for the treatment of prostate cancer", Oncol Rep. Aug. 2009, 22 (2):321-6. PMID: 19578772.
Brady et al (A pilot study in intraparenchymal therapy delivery in the prostate: a comparison of delivery with a porous needle vs. standard needle. BMC Urology (2018) 18:66) (Year: 2018). https://doi.org/10.1186/s12894-018-0378-8. 8 pages.
Cancaster—https://www.vitalitymedical.com/blog/selecting-syringes-and-needles.html; 2015.

(Continued)

*Primary Examiner* — Patrick T Lewis
(74) *Attorney, Agent, or Firm* — Squire Patton Boggs (US) LLP

(57) ABSTRACT

Minimally invasive treatment methods for benign prostatic hyperplasia (BPH) tissue. The methods including a composition comprising a cytostatic or cytotoxic drug delivered locally into the prostate at multiple locations within the prostate to produce an efficacious outcome for treating BPH.

20 Claims, 5 Drawing Sheets

(56) References Cited

U.S. PATENT DOCUMENTS

| | | | |
|---|---|---|---|
| 2023/0248688 A1 | 8/2023 | Trollsas et al. |
| 2024/0115544 A1 | 4/2024 | Trollsas et al. |
| 2024/0382447 A1 | 11/2024 | Trollsas et al. |
| 2025/0041207 A1 | 2/2025 | Trollsas et al. |

FOREIGN PATENT DOCUMENTS

| | | |
|---|---|---|
| JP | 49-115394 A | 11/1974 |
| JP | 2021-107061 A | 7/2021 |
| WO | WO 2009/060473 A2 | 5/2009 |
| WO | WO 2016/013829 A1 | 1/2016 |
| WO | WO 2018/128173 A1 | 7/2018 |
| WO | WO 2021/050953 A1 | 3/2021 |
| WO | WO 2022/067309 A1 | 3/2022 |
| WO | WO 2023/147080 A1 | 8/2023 |
| WO | WO 2025/013686 A1 | 1/2025 |

OTHER PUBLICATIONS

*Celltrion, Inc.* v. *Chugai Seiyaku Kabushiki Kaisha, Genetech, Inc.*, PTTAB, IPR2022-00579, U.S. Pat. No. 10,874,677 B2, Aug. 29, 2023, 29 pages.
Cilurzo et al., "Injectability Evaluation: an Open Issue", AAPS PharmSciTech, vol. 12, No. 2, Jun. 2011, pp. 604-609; DOI: 10.1208/s12249-011-9625-y.
De Bono JS et al. Gupta 8, Sartor AO; TROPIC Investigators. Prednisone plus cabazitaxel or mitoxantrone for metastatic castration-resistant prostate cancer progressing after docetaxel treatment: a randomised open-label trial. Lancet. Oct. 2, 2010;376(9747):1147-54. doi: 10.1016/S0140-6736(10)61389-X. PMID: 20888992.
Dhingra N. and Bhagwat D., "Benign prostatic hyperplasia: an overview of existing treatment.", Indian J Pharmacol. Feb. 2011; 43(1):6-12; doi: 10.4103/0253-7613.75657. PMID: 21455413; PMCID: PMC3062123.
*Ex Parte Gerald J. Bruck and Ahmed Kamel*, PTTAB, Appeal 2017-010719, U.S. Appl. No. 14/071,774, filed Jul. 30, 2018, 11 pages.
In re Young, United States Court of Customs and Patent Appeals. | Mar. 25, 1935 | 22 C.C.P.A. 1060, 75 F.2d 996, 25 USPQ 69 (CCPA 1935).
Jackson et al., "The Suppression of Human Prostate Tumor Growth in Mice by the Intratumoral Injection of a Slow-Release Polymeric Paste Formulation of Paclitaxel", Cancer Research 60, pp. 4146-4151, Aug. 1, 2000.
Koshkin et al., "Randomized phase II trial of neoadjuvant evero. limus in patients with high-risk localized prostate Cancer", Investigational New Drugs 37, 2019, pp. 559-566; doi: 10.1007/510637-019-00778-4.
Le Broc et al (Development of innovative paclitaxel-loaded PLGA nanoparticles: Study of their antiproliferative activity and their molecular interactions on prostatic cancer cells. International Journal of Pharmaceutics 454, 2013, pp. 712-719.
Lesovaya et al., "Rapatar, a nanoformulation of raparnycin, decreases chemicallyinduced benign prostate hyperplasia in rats", Oncotarget, 2015, vol. 6, No. 12, pp. 9718-9727.
Li, Jun, et al. "Synaptic P-Rexl signaling regulates hippocampal long-term depression and autism-like social behavior." Proceedings of the National Academy of Sciences 112.50 (2015): E6964-E6972.
Li, Shidong, et al. "Dosimetric and technical considerations for interstitial adenoviral gene therapy as applied to prostate cancer." International Journal of Radiation Oncology" Biology" Physics 55.1 (2003): 204-214.
Liu et al., "Roles of autophagy in androgen-induced benign prostatic hyperplasia in castrated rats", Experimental and Therapeutic Medicine, 2018, 15: 2703-2710.
Lu et al., "Raparnycin-induced autophagy attenuates hormone-imbalance-induced chronic non-bacterial prostatitis in rats via the inhibition of NLRP3 inflammasorne-rnediateci inflammation", Molecular Medicine Reports 19, 2019, pp. 221-230.
Melo, Gustavo Barreto, et al. "Critical analysis of techniques and materials used in devices, syringes, and needles used for intravitreal injections." Progress in Retinal and Eye Research 80 (2021): 100862.
Pal SK et al., "Critical appraisal of cabazitaxel in the management of advanced prostate cancer", Clinical Interventions in Aging, 2010, vol. 5, pp. 395-402; doi: 10.2147/CIA.S14570.
Sartor, "Eligard® 6: a New Form of Treatment for Prostate Cancer", European Urology Supplements 5, 2006, pp. 905-910.
Shikanov et al. "Intratumoral Delivery of Paclitaxel for Treatment of Orthotopic Prostate Cancer", Journal of Pharmaceutical Sciences, vol. 98, No. 3, Mar. 1, 2009, pp. 1005-1014, XP055509946.
Watt et al., "Injectability as a function of viscosity and dosing materials for subcutaneous administration", International Journal of Pharmaceutics, vol. 554, 2019, pp. 376-386.
Yared et al., "Update on taxane development: new analogs and new formulations", Drug Design Development and Therapy, 2012, vol. 6, pp. 371-384. doi: 10.2147/DDDT.528997.

* cited by examiner

Needle track, urethra distance, 1st location, unit volume

*DDD + Syringe Needle*

TREATING BENIGN PROSTATIC HYPERPLASIA

FIELD

Minimally invasive, local treatments for men's health and, more particularly, lower urinary tract symptoms.

BACKGROUND

Benign Prostatic Hyperplasia (BPH) is a noncancerous increase in size of the prostate gland due to proliferation of glandular epithelial tissue, smooth muscle and connective tissue within the prostate transition zone that causes lower urinary tract symptoms. Lower urinary tract symptoms (LUTS) include voiding or obstructive symptoms such as hesitancy, poor and/or intermittent stream, straining, feeling of incomplete bladder emptying, and storage or irritative symptoms such as frequency, urgency, urge incontinence, and nocturia. It affects approximately half of men aged 50 and over and by age 80, 90% of men are affected. Treatment options consist of lifestyle changes, medications, various procedures, and surgery. Lifestyle changes consist of weight loss, exercise, and decreased caffeine consumption. With more significant symptoms, oral medications such as alpha blockers (e.g., terazosin) or 5-alpha-reductase inhibitors (e.g., finasteride) are prescribed. These medications, requiring daily dosing for patient compliance, may require a long onset to show efficacy, if at all, and carry side effects such as ejaculation changes, erectile dysfunction, weakness, headaches, and decreased libido.

Lower urinary tract symptoms (LUTS) may be assessed in two ways: International Prostate Symptom Score (IPSS) and measuring a flow rate or Qmax. The IPSS is generated from patient responses from a series of questions indicating whether the patient is experiencing LUTS. Higher IPSS reflect a patient that is suffering more from BPH symptoms, while a lower IPSS reflect a patient suffering less of these symptoms, i.e., more normal functioning.

Prostate and urinary flow health is also measured by Uroflow or Uroflowmetry, which is a test to measure flow (rate) of micturition. During the test, a uroflow device, a Uroflow meter, tracks urine flow in mL/sec. It reports Urination volume, meaning, how much urine flows out. Qmax is the value of the highest flow rate measured during the test. In other words, Qmax is the fastest stream measured in mL/s. Low Qmax value is commonly a sign of obstruction. It is a common symptom of BPH. Normal urine flow rate is about 16 ml/sec or higher.

There is an unmet clinical need to treat BPH with improved and sustained efficacy, administered via a less invasive procedure and with less associated side effects.

SUMMARY

The disclosure is generally directed to a local delivery of sustained release formulation for efficacious treatment of a target tissue associated with the prostate, and/or providing relief of urinary tract symptoms originating from or associated with an enlarged prostate while mitigating if not avoiding damage to nearby prostate structures or the urethra. The treatment may be used by itself, or in combination with other known treatments.

In one aspect, provided herein are methods for treating Benign Prostatic Hyperplasia (BPH). In certain embodiments, the methods comprise the steps of penetrating the subject's prostate with a needle syringe to form a first needle track, withdrawing the needle syringe from the first needle track to provide a first location in the needle track for dispensing a composition, and dispensing no more than a first unit volume of the composition into the first location. In certain embodiments, the methods further comprise the steps of penetrating the prostate with a needle syringe to form a second needle track spaced from, and on an opposite side of the subject's urethra from the first needle track, withdrawing the needle syringe from the second needle track to provide a second location in the second needle track for dispensing the composition, and dispensing no more than a second unit volume of the composition into the second location. In certain embodiments, the composition comprises an effective amount of a cytotoxic or cytostatic drug and a water-soluble solvent capable of dissolving the drug into the subject's prostate. The subject can be any subject having BPH. The syringe can be any syringe deemed useful by the practitioner of skill. Useful syringes are described herein. Each needle track is formed by withdrawing, for instance partially withdrawing, the needle syringe from the penetrated tissue. The unit volume can be any unit volume deemed useful by the practitioner of skill. Useful unit volumes are described herein. Useful compositions are described herein.

In another aspect, provided herein are methods for treating Benign Prostatic Hyperplasia (BPH). In certain embodiments, the methods comprise the steps of forming a needle track in the subject's prostate with a needle syringe, withdrawing the needle syringe from the needle track to provide a first location in the needle track, and dispensing a first unit volume of a composition into the first location. In certain embodiments, the methods further comprise withdrawing the needle syringe from the needle track to provide a second location in the needle track, and dispensing a second unit volume of the composition into the second location. In certain embodiments, the composition comprises an effective amount of a cytotoxic or cytostatic drug and a water-soluble solvent capable of dissolving the drug in the subject's prostate. The subject can be any subject having BPH. The syringe can be any syringe deemed useful by the practitioner of skill. Useful syringes are described herein. Each needle track is formed by withdrawing, for instance partially withdrawing, the needle syringe from the penetrated tissue. The unit volume can be any unit volume deemed useful by the practitioner of skill. Useful unit volumes are described herein. Useful compositions are described herein.

In another aspect, provided herein are methods for treating Benign Prostatic Hyperplasia (BPH). In certain embodiments, the methods comprise the steps of forming a needle track in the subject's prostate using a needle syringe, withdrawing the needle syringe, and dispensing at least one unit volume of a composition into a first location of the needle track, wherein the dispensing the at least one unit volume into the location is completed at least 10 to 15 mm or at least 15 mm from the prostate apex, and/or wherein the dispensing the at least one unit volume into the location is completed at least 7 to 10 mm or at least 10 mm from the verumontanum. In certain embodiments, the composition comprises an effective amount of a cytotoxic or cytostatic drug and a water soluble solvent capable of dissolving the drug into a prostate transition zone. The subject can be any subject having BPH. The syringe can be any syringe deemed useful by the practitioner of skill. Useful syringes are described herein. Each needle track is formed by withdrawing, for instance partially withdrawing, the needle syringe from the penetrated tissue. The unit volume can be any unit volume deemed useful by the practitioner of skill. Useful unit volumes are described herein. Useful compositions are described herein.

In another aspect, provided herein are methods for treating Benign Prostatic Hyperplasia (BPH). In certain embodiments, the methods comprise forming a needle track in the subject's prostate using a needle syringe, withdrawing the needle syringe to provide a first location in the needle track, and dispensing no more than one unit volume into the first location of the needle track, wherein the dispensing the at least one unit volume into the first location is initiated no closer than 3 to 5 mm or 7 to 10 mm or 10 mm from the subject's bladder neck or prostate base. In certain embodiments, the composition comprises an effective amount of a cytotoxic or cytostatic drug and a water-soluble solvent capable of dissolving the drug into a prostate transition zone. The subject can be any subject having BPH. The syringe can be any syringe deemed useful by the practitioner of skill. Useful syringes are described herein. Each needle track is formed by withdrawing, for instance partially withdrawing, the needle syringe from the penetrated tissue. The unit volume can be any unit volume deemed useful by the practitioner of skill. Useful unit volumes are described herein. Useful compositions are described herein.

In another aspect, there is also disclosed an apparatus for prostate treatment. The apparatus comprises a needle syringe, a dose dispensing device and the composition contained within the syringe. In certain embodiments, the methods are carried out with means for dispensing the composition.

Prostate treatment according to the disclosure may be described as a prostate treatment having at least the following characteristics: minimal uncontrolled drug diffusion and the administration of several small implants directly into the prostate BPH or transition zone using a needle syringe, and in some instances the anterior zone or peripheral zone as well.

In certain embodiments, the treatment comprises the delivery of the drug or drugs in the composition. In certain embodiments, the treatment further comprises delivery of one or more additional drugs to treat the BPH. In certain embodiments, the treatment may be used with, or in addition to treatments involving removal/ablation of tissue, and/or delivery of energy to the tissue and additionally the administering of various agents. Methods according to the disclosure may additionally, or alternatively, be administered before a treatment of BPH according to other methods. Methods according to the disclosure may additionally, or alternatively, be administered after a treatment of BPH according to other methods. Methods according to the disclosure may additionally, or alternatively, be administered before and after a treatment of BPH according to other methods.

In another aspect, provided herein is a system for treating BPH including a needle syringe, the composition including the therapeutic drug, and imaging device for locating a target tissue of the prostate. The imaging device, e.g., ultrasound, may be used both as a needle guide to the target tissue and for sizing the prostate. Once prostate size is determined, the number of implants needed to produce an efficacious outcome is determined. The implant size may be accurately dispensed using a means for dispensing a small unit volume into the prostate.

Treatment of BPH by a needle injection, in a small quantity at a plurality of locations in the target tissue, offers several benefits over other methods. Among the benefits are less invasive procedures leading to greater patient acceptance and less complications during patient treatment, less frequent procedures needed, and reduced incidence of drug affecting nearby tissue leading to such outcomes as adverse consequences for urinary or sexual function.

BRIEF DESCRIPTION OF THE DRAWINGS

FIG. 4 also shows relative distances between portions of the needle track and urethra. Ideally one wants the same distance along the needle track, but the urethra is not generally straight and/or a medical professional may encounter some difficulty in making a parallel needle track to urethra. In these cases there may be a prescribed maximum and minimum distance advisable to have a desired effect and to avoid adverse effects on the urethra. In certain embodiments the maximum distances and minimum distances of the needle track relative to the urethra may be prescribed as 10 mm or 15 mm (max), and 3 to 5 mm (min).

DETAILED DESCRIPTION

Definitions

Figure 1:
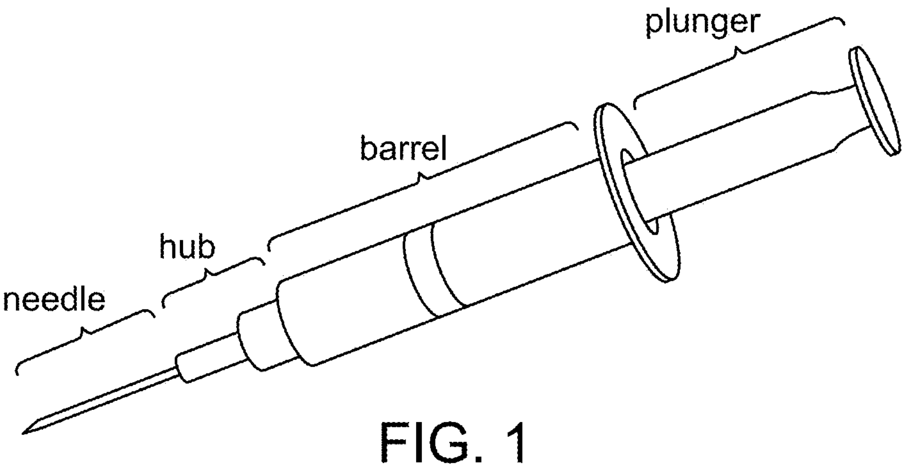
FIG. 1 (PRIOR ART)
FIG. 1 is a needle syringe.

For purposes of this disclosure, the following terms and definitions apply:

The following are examples of the polymer naming nomenclature appearing in the listing of additional disclosed embodiments following the detailed description. Generally, the format is polymer or abbreviation, monomer ratio, and end-cap abbreviation. Useful polymers and abbreviations are described herein. The monomer ratio typically is in percents. End-cap groups include acid (A) and ester (E). Other examples not explicitly spelled out here use the same rationale: PLGA8515A (0.3 dl/g) means poly(lactide-co-glycolide) with a monomer ratio of 85/15, end capped with an acid group (A), and an inherent viscosity of 0.3 dl/g; and PLGA6535E (0.5 dl/g) means poly(lactide-co-glycolide) with a monomer ratio of 65/35, end capped with an ester groups (E), and an inherent viscosity of 0.5 dl/g; and PLGA5050A (0.2 dl/g) means poly(lactide-co-glycolide) with a monomer ratio of 50/50, end capped with an acid group (E), and an inherent viscosity of 0.2 dl/g; and Poly (lactide-co-glycolide) is typically poly(D,L-lactide-co-glycolide) but could also be e.g. any or a mixture of poly(D, L-lactide-co-glycolide), poly(D-lactide-co-glycolide), and poly(L-lactide-co-glycolide).

The terms "about" or "approximately" is defined herein as 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, dl is about d2 means dl is 30%, 20%, 15%, 10%, 5%, 4%, 3%, 2%, 1.5%, 1%, 0% or between 1-2%, 1-3%, 1-5%, or 0.5%-5% different from d2. If dl is a mean value, then d2 is about d1 means d2 is within a one-sigma, two-sigma, or three-sigma variance from dl. It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

The term "cytostatic" as used herein refers to a drug that is non-toxic to cells but does mitigate cell proliferation and permit cell migration. Cytostatic drugs may include without limitation rapamycin, sirolimus, everolimus, zotarolimus, myolimus, temsirolimus, tacrolimus, macrolide antibiotics, ridaforolimus, biolimus, novolimus, deforolimus, structural derivatives and functional analogues of rapamycin and any macrolide immunosuppressive drug. mTOR/PI3K dual inhibitors may also be utilized including dactolisib, BGT226, SF1126, PKI-587, and NVPBE235, mTORC1/mTORC2 dual inhibitors may also be utilized including sapanisertib, AZD8055, AZD2014 as derived from morpholino pyrazolopyrimidine.

The term "cytotoxic" as used herein refers to a drug that causes cell death and atrophy and inhibits cell growth and proliferation. These drugs may include but are not limited to paclitaxel, taxanes, protaxel, vincristine, etoposide, nocodazole, indirubin, anthracycline derivatives, daunorubicin, daunomycin, tauromustine, bofumustane, carboplatin, carmustine, cisplatin, docetaxel, capecitabine, carmofur, tegafur, doxifluridine (5'-DFUR), cabazitaxel, 5-fluorouracil, gemcitabine, mitomycin, procarbazine, and plicamycin. These drugs may also be apoptotic such as TGF, topoisomerase inhibitors, including, 10-hydroxycamptothecin, irinotecan, and doxorubicin.

The term "absolute viscosity" as used herein means the viscosity measured relative to the viscosity of a known substance. Unless stated otherwise "absolute viscosity" (as compared to inherent viscosity) is represented by the symbol p. Absolute viscosities may be measured using a calibrated digital rotational viscometer spindle (no. 1 size) with 10 mL solutions in 40 ml polypropylene vials with an approximately 50% submerged spindle solution contact, with measurements made at room temperature conditions.

When expressing a % of a substance included in the composition, the % of that substance may be expressed in terms of a percent weight of the drug(s) to the overall weight of the SRF ("% X by wgt"), or to the overall volume of the SRF ("% X by vol"). Unless stated otherwise the percent dosage % will, by default, always refer to a % by weight to the total measured SRF. Unless stated otherwise, weights are given in grams ("g") or milligrams ("mg"), molecular weight in kilo-Daltons ("kDa"), volume in microliters ("μL") or milliliters ("mL"), and viscosity units are expressed as inherent viscosity (i.e., the ratio of the natural logarithm of the relative viscosity to the mass concentration of the substance, such as a polymer. The unit of inherent viscosity is deciliters per gram (dL/g). A different measure of viscosity is intrinsic viscosity, which is a measure of a solute's contribution to the total viscosity. Another viscosity is dynamic viscosity or absolute viscosity, the units of which are centimeter-gram-seconds, also known as centipoise (cP).

The term "needle syringe" refers to a needle, and where appropriate, an attached syringe. The needle can be used, for instance, to penetrate tissue, to form a needle track, and to dispense a composition. The syringe is useful, for instance, for containing and dispensing the composition.

The terms "dispensed or dispensing", "injected or injecting", or "implanted or implanting" all carry the same meaning, which is having placed or placing, respectively, a volume of composition directly into the prostate using a needle.

"Imaging device" refers to any device that can render one or more cross-sectional images of the prostate (e.g., two views—transverse and sagittal) using, e.g., acoustic or magnetic wave energy. For example, an acoustic wave imaging device commonly used during prostate biopsies is a Trans-Rectal UltraSound (TRUS) device. A Magnetic Radiation Imaging (MRI) device may be used to model the prostate before or after treatment.

A "transverse view" view is obtained during TRUS as a cross-sectional image displaying the prostate's height and width and symmetry from base to the apex.

Figure 2A:
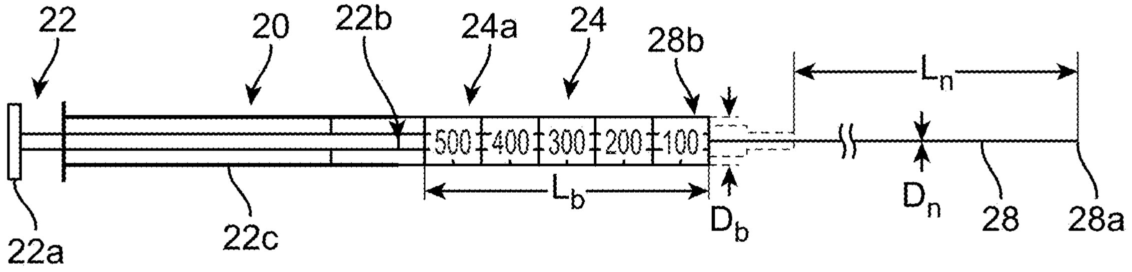
FIGS. 2A, 2B are more detailed side views of the needle syringe of FIG. 1.
Figure 2B:
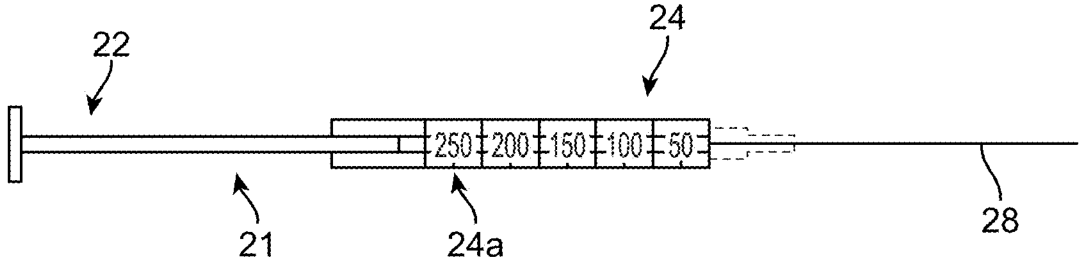

A "sagittal view" obtained during TRUS is a side-view of the prostate that shows its length and position relative to the bladder and urethra. FIGS. 2A and 2B show transverse and sagittal views, respectively, of the prostate.

The term "sustained release formulation (SRF)" as used herein refers to a substance for treating BPH, the substance including a drug (or drugs), solvent for the drug and carrier for the drug(s) or drug carrier comprising a polymer composition administered to the target tissue in liquid, gel or solid form using a delivery vehicle, such as a needle syringe, whereupon local delivery of the composition (comprising the SRF) to the target tissue the SRF is effective in producing a sustained release of the drug(s) to the targeted tissue of the prostate, thereby producing an efficacious result over a period of time, e.g., from 14 days, 30 days, 1 to 3 months, up to 6 months, up to 12 months, or up to 2 years following treatment and with minimal uncontrolled drug diffusion. Other substances may also be present in the composition (e.g., an ultrasound/echoing enhancing medium or other imaging enhancing depending on the imaging modality used). A programmed, sustained release of, e.g., from 14 days or 1 to 12 months for substantially all of the drug to dissipate from the carrier is achieved by selection of drug carrier (polymer composition) and/or modifying the morphology and mechanical properties, the polymer/drug ratio, and controlling the physical shape/dimensions (volume) of the SRF and/or composition that is delivered to the target tissue. Other factors influencing a release rate are described in greater detail, below.

The term "composition" as used herein means a product of mixing or combining various elements or ingredients. Whenever the word "composition" is used, it will be understood that the composition includes, at a minimum, a cytotoxic or cytostatic drug and solvent capable of dissolving the drug. A sustained release formulation (SRF) is a composition that also includes a polymer. The term "polymer composition" however is not a composition that includes a drug or solvent for the drug.

Methods

In certain embodiments, the subject has an IPSS score deemed suitable for treatment by the practitioner of skill. In certain embodiments, the subject has an IPSS score greater than or equal to 13. In certain embodiments, the subject has an IPSS score greater than or equal to 20. In certain embodiments, the subject has an IPSS score greater than or equal to 25.

In certain embodiments, the methods comprise the steps of penetrating the subject's prostate with a needle syringe to form one or more needle tracks. The needle syringe is withdrawn or partially withdrawn to provide a location in the needle track for dispensing a composition.

In particular embodiments, partial withdrawal of the needle syringe provides a location within the needle track. The composition can be dispensed into this location. In certain embodiments, the needle syringe is partially withdrawn once to provide one location in the needle track. In certain embodiments, the needle syringe is partially withdrawn twice to provide two locations in the needle track. In certain embodiments, the needle syringe is partially withdrawn three times to provide three locations in the needle track. In certain embodiments, the needle syringe is partially withdrawn four times to provide four locations in the needle track. In certain embodiments, the needle syringe is partially withdrawn more than four times to provide more than four locations in the needle track.

In certain embodiments, the prostate is penetrated one time with a needle syringe. In certain embodiments, the prostate is penetrated more than one time with one or more needle syringes. In certain embodiments, the prostate is penetrated two times with one or more needle syringes. In certain embodiments, the prostate is penetrated three times with one or more needle syringes. In certain embodiments, the prostate is penetrated four times with one or more needle syringes. In certain embodiments, the prostate is penetrated more than four times with one or more needle syringes. In certain embodiments, the needle syringes are different. In certain embodiments, the prostate is penetrated each time with the same needle syringe. With each penetration, the needle syringe may be withdrawn to provide one or more than one locations for dispensing the composition, as described above.

At each location, a unit volume of the composition is dispensed into the location with the needle syringe. The unit volumes may be the same, or they may be different. Useful unit volumes are described herein.

Access to prostatic tissue may be achieved in a transurethral, transrectal or transperineal manner via an existing body orifice. Access may be by more than one manner. It may be beneficial and less invasive to access the tissue by transurethral, transrectal or transperineal approaches. The advantages with a transrectal or transperineal approach include one or more (1) oral and/or local anesthesia application instead of general anesthesia, (2) less trauma to the urethra tract and less resulting side effects also reducing the need for catheterization, (3) faster recovery time for the patient, (4) familiar treatment for the urologist physician similar to prostate cancer biopsy. For access by transrectal or transperineal approach, guidance may be provided by ultrasound, x-ray, computed tomography, magnetic resonance imaging or other imaging modality. Ultrasound imaging using a TRUS device may be beneficial given that ultrasound is utilized for prostate biopsy. The transrectal approach closely mirrors the present prostate ultrasound and biopsy techniques familiar to urologists. Transrectal and transperineal approaches both avoid interaction with the urethra, which limits the caustic effects of urethral procedures therefore minimizing side effects and dysuria associated with currently available BPH procedures.

In certain embodiments, the methods comprise the steps of penetrating the subject's prostate with a needle syringe to form a first needle track. The methods further comprise withdrawing the needle syringe from the first needle track to provide a first location in the needle track for dispensing the composition. The methods further comprise dispensing no more than a first unit volume of the composition into the first location. In certain embodiments, the methods further comprise penetrating the prostate with a needle syringe to form a second needle track spaced from, and on an opposite side of the subject's urethra from the first needle track. The methods further comprise withdrawing the needle syringe from the second needle track to provide a second location in the second needle track for dispensing the composition. The methods further comprise dispensing no more than a second unit volume of the composition into the second location.

In certain embodiments, no portion of the first or second needle track is located nearer than 5 mm from the subject's urethra. In certain embodiments, the first location is located on an anterior side of the subject's prostate. In certain embodiments, the first location is at least partially contained within a prostate transition zone.

In certain embodiments, a plurality of unit volumes of the composition comprising the first unit volume are dispensed into a respective plurality of locations comprising the first location in the first needle track.

In certain embodiments, the plurality of unit volumes is dispensed by the following steps performed in the following order: partially withdrawing the needle from the first needle track to provide a second of the plurality of locations in the needle track for dispensing the composition after the first unit volume is dispensed into the first location, and dispensing no more than a second of the plurality of unit volumes into the second of the plurality of locations, and partially withdrawing the needle from the first needle track to provide a third of the plurality of locations in the needle track for dispensing the composition after the second of the plurality of unit volumes is dispensed into the second of the plurality of locations, and dispensing no more than a third of the plurality of unit volumes into the third of the plurality of locations. In certain embodiments, first of the plurality of unit volumes, second of the plurality of unit volumes, and third of the plurality of unit volumes have the same volume or different volumes.

In certain embodiments, the method further comprises the following steps performed in the following order: penetrating the prostate with a needle syringe to form a third needle track, withdrawing the needle from the third needle track to provide a third location in the third needle track for dispensing the composition, and dispensing no more than a third unit volume of the composition into the third location. In certain embodiments, the method further comprises following steps performed in the following order: penetrating the prostate with a needle syringe to form a fourth needle track, withdrawing the needle syringe from the fourth needle track to provide a fourth location in the fourth needle track for dispensing the composition, and dispensing no more than a fourth unit volume of the composition into the fourth location.

In certain embodiments of any of the methods described herein, the unit volume is between 5 μl and 25 μl and the drug is paclitaxel, or from 25 μl up to 100 μl, 200 μl, 250 μl, 250 μl or 300 μl and the drug is paclitaxel. In certain embodiments of any of the methods described herein, the unit volume is between 5 μl and 10 μl, 10 μl and 25 μl, 25 μl and 50 μl, or 50 μl and 100 μl and the drug is a cytotoxic drug such as paclitaxel. In certain embodiments of any of the methods described herein, the unit volume is 5 μl, or between 5 μl and 10 μl, or between 20 μl and 30 μl, or between 30 μl and 70 μl, or between 10 μl and 15 μl and the drug is a cytotoxic drug such as paclitaxel or docetaxel. In certain embodiments of any of the methods described herein, the unit volume is 10 μl and the drug is paclitaxel. In certain embodiments of any of the methods described herein, the unit volume is 15 μl and the drug is paclitaxel. In certain embodiments of any of the methods described herein, the unit volume is 20 μl and the drug is paclitaxel or docetaxel. In certain embodiments of any of the methods described herein, the unit volume is 25 μl and the drug is paclitaxel or docetaxel.

Needle Syringe & Dose Delivery Device

The dose delivery device can be any drug delivery device deemed suitable by the practitioner of skill. In certain embodiments, the drug delivery device is one described in any of international patent applications WO 2025/136860, WO 2023/147080, and WO 2022/067309, the contents of which are hereby incorporated by reference in their entireties. Generally, the drug delivery device comprises a syringe and a needle syringe, loaded with the composition. One example of a dose delivery device is shown and described in connection with FIG. 6. Additionally, useful compositions are described herein. In certain embodiments, the composition is delivered with means for delivery.

FIG. 1 depicts an exemplary needle syringe. FIGS. 2A, 2B depict aa more detailed view of the needle syringe of FIG. 1. Needle syringes such as the ones in FIG. 1 and FIGS. 2A-2B are used to deliver multiple unit volumes of a composition, e.g., from 5, 10 or 25 microliters at a time, to the prostate transition zone when assembled with the dose delivery device of FIG. 6. The needle syringe is characterized by a relatively long and narrow needle (for example, a 15 and 20 cm in length needle, and 0.02 cm to 0.12 cm needle lumen, alternatively a needle having a slenderness ratio, defined as needle length divided by lumen diameter, of between 200 and 400 or, preferably, 250 and 340). A long, narrow needle (e.g., 20 cm with 0.06 cm lumen size) is desired as the manner for delivering the composition to the target tissue. Because it is a less invasive approach to accessing the target tissue than other methods for treating BPH and is more likely to be acceptable by patients in general.

Referring to FIGS. 2A-2B, a typical needle syringe 20 includes an applicator portion 22 with a plunger 22*a*, a plunger head 22*b*, a barrel 24, and a hub portion 22*d* that connects a needle 28 with an interior chamber of the barrel 24 and forms a fluid-tight connection for passage of a fluid contained within the barrel 24 through the needle lumen. The needle syringes depicted in FIGS. 2A-2B have sizes for holding and dispensing a unit volume through a long, narrow needle tip 28*a*. The needle 28 is characterized by a length $L_n$ and lumen diameter $D_n$ (the hub portion 22*d* is shown in phantom for the sake of illustrating the measured length $L_n$, which is taken from upstream opening 28*b* forming a fluid-tight connection between the barrel 24 and needle 28 and the needle tip 28*a* that first punctures the skin). The needle 28 may be made from stainless steel. The needle syringe 20 in FIG. 2A shows by example gradations of 500/400/300/200/100 micro-liters for dispensing unit volumes of e.g., 0.05 ml (50 micro-liters). The barrel capacity is 500 micro-liters. The barrel 24 has a length $L_b$ and barrel inner or lumen diameter $D_b$. A prefilled syringe barrel (500 micro-liter) may have attached to it a needle length $L_n$ of 20 cm, and the barrel 24 may have a 150-200 micro-liter dead volume. The syringe 20, which may need to be prefilled, may also incorporate a stabilizer 22*c* for guiding the plunger head 22*b* towards the needle opening 28*b*. The composition comprising the SRF (contained in the syringe barrel 24 in amounts up to about 500 micro-liters) is ejected through the needle tip 28*a* by finger pressure applied to the plunger head 22*b*. In this example, the barrel 24, when holding 500 micro-liters of composition with a 150 micro-liter dead volume can hold up to 7, 50 micro-liter unit volumes. The needle syringe 21 in FIG. 2B is the same in several respects as the syringe in FIG. 2A, except that it has instead a 250 micro-liter barrel capacity. The needle syringe 21 may also incorporate a stabilizer 22*c* as in FIG. 2A. In another example a 250 micro-liter capacity syringe has graduations of 50 uL, 25 uL, 5 uL and 2.5 uL to help with more accurately dispensing low unit volumes of the composition.

The syringe may be pre-filled to hold a sufficient total volume for fully treating a patient (e.g., 4 or more unit volumes composition at different locations in the prostate tissue). In some embodiments, an applicator portion may include syringe chambers for holding the SRF drug and drug carrier separate from each other, a mixing element for combining the drug and drug carrier such as a static mixing Y-adapter that feeds into a narrow and long, or high slenderness (L/D) ratio needle 28. Alternatively, the drug, drug carrier, and solvent may be mixed using two syringes connected with an adapter, with back and forth plunging to mix the drug, drug carrier, and polymer. The applicator portion may have markings demonstrating measurement of lengths of needle insertion or composition volume.

The needle length $L_n$ may be from 10 to 30 cm, preferably from 15 to 20 cm. The lumen diameter $D_n$ may be 0.06 cm, or between 0.06 and 0.08 cm, and in some embodiments 0.02 cm up to 0.12 cm. The needle's slenderness ratio ($L_n/D_n$) may be between 200 and 400, or between 250 and 350. The barrel length $L_b$ may be from 5 to 20 cm, preferably from 5 to 10 cm. The barrel lumen diameter $D_b$ may be 0.2 to 0.5 cm. In some embodiments, the syringe barrel's slenderness ratio ($L_b/D_b$ may be 5 and 50, or between 10 and 30) is an important factor to consider. Barrel slenderness ratios in these ranges were found to help with more accurately dispensing low unit volumes of the composition.

In some embodiments, the composition with SRF can be provided to a health professional in the form of a polymer injectate and drug powder in separate delivery syringes and mixed on or about the time of treatment and placed into the syringe barrel. This would allow for a mostly or partially crystalline drug directly into the injectate to increase drug retention time and exposure time and reduce systemic drug loss given that some drug would remain in a powdered crystalline form after user preparation.

Figure 6:
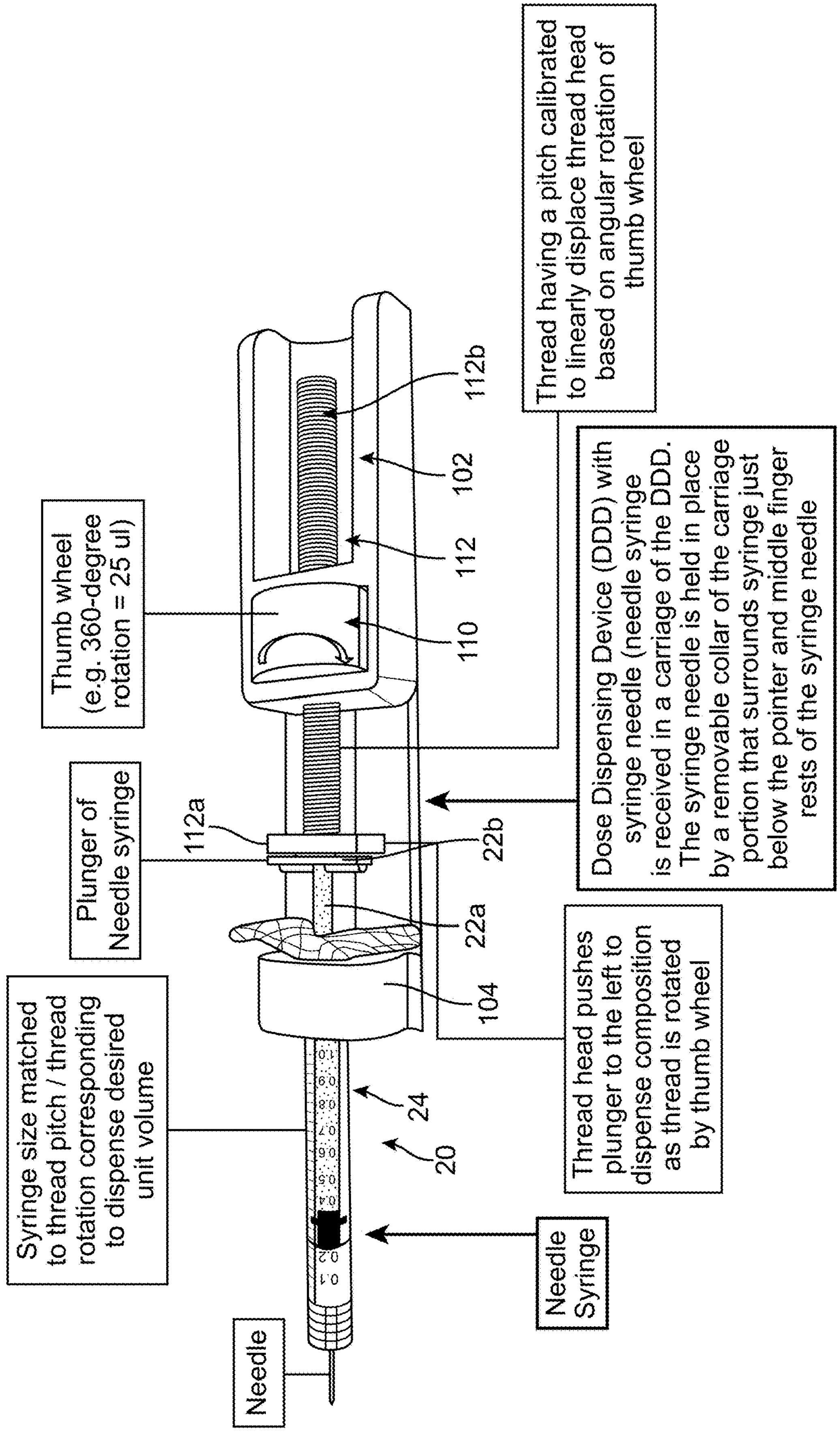
FIG. 6 is perspective view of an example of an assembly of dose dispensing device (DDD) and a syringe needle. The DDD is used to provide a dispensing of a desired unit volume implant size from the syringe needle according to, in this example, a rotation of a wheel through an angle corresponding to the desired unit volume size dispensed from the needle.

Reference is now made to an assembly of the needle syringe 20 of FIG. 2A and Dose Dispensing Device (DDD) 100 in FIG. 6. Referring to FIGS. 2A and 6, The needle syringe 20 is received and restrained within a carriage 102 of the DDD, which includes a latching portion 104 that grips the barrel of the needle syringe below its finger rests so that the syringe plunger 22*a* may be moved relative to the barrel 24 by thread head 106 pushing against the plunger 22*a* to dispense composition from the tip of the needle 28. The needle syringe plunger 22*a* abuts thread head 112*a* of an arm 112, which is threaded and engages with a thumb wheel 110 used to dispense composition. Thread pitch 112*b* is selected to have an angular rotation of the thumb wheel 110 matched to a lateral (right to left in FIG. 6) displacement of the thread head 112*a* for the needle syringe barrel size corresponding to the desired unit volume implant volume (e.g., thread pitch 112*b* such that a 360 degree rotation of the thumb wheel 110 corresponds to a 25 μl unit volume dispensed from the needle syringe 20). The arm 112 moves laterally only by rotation of the thumb wheel 110. Fluidic resistance or backpressure trending to back-drive the thread head is prevented. Only rotation of the wheel 110 causes the thread head 112*a* to move laterally from left to right or right to left in FIG. 6.

In particular embodiments, the health professional (HP) holds in one hand the assembled syringe needle and DDD with thumb resting on thumb wheel 110. According to one method of treatment, after the needle track is formed, the needle is withdrawn to make a first location for dispensing a first unit volume in the prostate. The needle is held in position at the first portion. The thumb wheel 110 is then rotated 360 degrees to dispense a 25 μl unit volume in the first portion. After completing the 360 degree rotation the HP waits from 0.5 sec to 30 sec, depending on the viscosity of the composition and/or the needle gauge used, then proceeds with further withdrawing the needle from the needle track to make a second location for dispensing composition or to completely remove the needle from the needle track. The needle is again held in place at the second location after the wheel is rotated through the angle corresponding to the unit volume dispensed.

In certain embodiments, devices devoid of an anti-back drive feature may be used. For example, devices providing a button to apply constant finger pressure, if needed, to prevent the needle syringe plunger 22 from reversing direction, may be used to dispense unit volumes. The button engages a spring-biased locking piece that engages the arm to prevent the arm and needle syringe plunger (in mating contact with the arm) from moving backwards while finger pressure is applied.

Another embodiment that has an anti-back-drive feature is a worm gear threadingly coupled to a worm and threaded rack. Similar to FIG. 6, the worm, worm gear and threaded rack forming a gear train is used instead of the threaded arm and wheel shown in FIG. 6. Another embodiment is to have a plunger of the needle syringe displaced by an electronically activated arm. According to this embodiment the arm is displaced by energizing an electromagnet coupled to the arm, which engages the needle syringe plunger.

Unit Volume

The term "unit volume" as used herein refers to the maximum volume (v) of composition for an individual injection when treating BPH. In most cases there is a plurality of unit volumes of a composition per patient. For example, there can be n=2, 3, 4, 5, 6, 6-10, 6-12, 8-12, 12-24, or more, depending on the size of the prostate and unit volume size. Herein, n is the number of unit volumes. The larger the size of the prostate, generally speaking, the higher the number of unit volumes dispensed from a needle at different locations of the prostate. Unit volumes may range between 5 μl and 10 μl, 10 μl and 25 μl, 25 μl and 50 μl, 50 μl and 100 μl, 100 μl and 150 μl, 150 μl and 200 μl, 200 μl and 250 μl, or 250 μl and 300 μl. In some embodiments unit volumes range between 10 μl and 50 μl. The same unit volume may be used throughout a subject's prostate during a single treatment. Or the unit volume may vary during the course of a single treatment. In either case, a treatment method will involve implanting several unit volumes, e.g., 2, 3, etc., in the prostate at opposite sides of the urethra.

Total Volume

The term "total volume" of composition (i.e., the total amount of composition injected into the prostate during a single treatment session, defined as within a 1-2 hours of, or within 24 hours from the start of a treatment session) is the total volume of composition administered to the patient and expected to produce an efficacious outcome when treating BPH, such as by a programmed sustained release of the drug from a sustained release formulation (SRF). This efficacious outcome may be measured using the International Prostate Symptom Score (IPSS), or more generally relieving lower urinary tract symptoms (LUTS) including voiding or obstructive symptoms such as hesitancy, poor and/or intermittent stream, straining, feeling of incomplete bladder emptying, and storage or irritative symptoms such as frequency, urgency, urge incontinence, and nocturia. A total volume is expected to produce 1-5%, 5-10%, 5-15%, 5%-25% or 5%-30% prostate volume reduction.

Implant Location

The term "implant location" refers to a specific region of the prostate visually distinguishable from other implant locations when viewing media generated from an imaging device. An implant location in the prostate may be distinguished from another implant location in the transverse view of the prostate. Or an implant location may be distinguished from another implant location in the sagittal view of the prostate, such as when multiple implants of a unit volume are placed at different axial locations along a single needle track as the needle is incrementally withdrawn from the needle track.

Determine Total Volume & Unit Volume for the Patient

Normal adult human prostates weigh approximately 20-25 g. A majority of BPH prostate sizes are 30 g or larger with most ranging between 25-100 g or 30-80 g. For prostate sized grams may be used equivalently to cubic centimeters or milliliters by assuming the density is the same as water. The total volume, or number (n) of unit volumes (v) injected per prostate may be variable and selected in proportion to the prostate size. Or there may be a selection among a predetermined number of total volumes or numbers of unit volumes for dispensing a total volume for prostates of any size, large or small. Two examples follow.

In certain embodiments, the treatment plan for the prostate is determined using measurements taken from imaging of the prostate using a transrectal ultrasound (TRUS) device. After enema preparation, conduct TRUS measurement of prostate (width, height, length) to determine volume (PV) and transition zone volume including verumontanum position if possible. Identify BPH region or transition zone for treatment. Place optional 16 Fr silicone Foley catheter to visualize the urethra and stabilize the prostate.

Safety Precautions on Label

The number of unit volumes implanted per needle track, when the same unit volume size is used throughout treatment, may be determined from one or both of the following methods when a constant unit volume is used throughout treatment. For example, when a unit volume is 50 μl, and given a measured Prostate Length (PL), the number of implants per needle tract is PL minus 2 (e.g. PL of 5 cm=5−2=3 implants). When a unit volume is 25 μl, for a given a measured Prostate Length (PL), the number of implants per needle tract is 2*(PL−2) (e.g. PL of 5 cm=2*(5−2)=6 implants). In these examples and other examples, implants are dispensed to avoid harm or adverse effects on the patient by having the drug either escape from the prostate or interact with nearby tissue. To this end, there should be minimum distances observed between the needle track and certain anatomical regions of the prostate to avoid adverse events such extrusion of the composition into the perineum as this may cause ejaculatory dysfunction or incontinence.

According to some embodiments, to avoid possible adverse effects the needle track length for 50 μL implants should be determined so that the first implant dispensed into the needle track is initiated at least 5 mm from the prostate base and the last implant dispensed into the needle track is initiated at least 25 mm from the prostate apex and finished at least 15 mm from the prostate apex. Or start the last implant at least 20 mm from the verumontanum and finished at least 10 mm from the verumontanum.

According to other embodiments, to avoid possible adverse effects the needle track length for 25 μL implants should be determined so that the first implant dispensed into the needle track is initiated at least 5 mm from the prostate base and the last implant dispensed into the needle track is initiated at least 20 mm from the prostate apex and finished at least 15 mm from the prostate apex. Or start the last implant at least 15 mm from the verumontanum and finished at least 10 mm from the verumontanum.

Other BPH Treatments

In contrast to the present disclosure, known methods for treating BPH require more invasive procedures, more frequent treatment due to diffusion of a drug into other areas, or more generalized treatment of BPH raising the possibility of adverse effects because a comparatively high dosage of the drug is needed to treat the area while accounting for leakage or diffusion of the drug to other areas. Adverse effects incurred by these other procedures may include diminished urinary or sexual function. It is desired to have an effective treatment targeting only the target tissue and nowhere else (e.g., avoiding the bladder, urethra and nerves surrounding the prostate) and to perform the procedure in a less invasive manner for patient acceptance. With these objectives in mind, the inventors sought to develop a formulation that could be delivered by way of local prostate needle injection and that could overcome the foregoing drawbacks with existing procedures for treating BPH.

Compositions

The composition comprises the drug or drugs and one or more pharmaceutically acceptable polymers. In certain embodiments, the composition is one described in any of international patent applications WO 2025/136860, WO 2023/147080, and WO 2022/067309, the contents of which are hereby incorporated by reference in their entireties. Useful compositions are further described herein.

The drug portion of the composition may be an anti-inflammatory, anti-proliferative, cytoreductive, cytostatic, and/or cytotoxic drug that would affect the prostate size and gland proliferation. In some embodiments the composition includes a “sustained release formulation (SRF)”. Once delivered to the target tissue, a drug may release from the SRF in a slow, sustained release fashion, optionally delivered as an initial burst of the drug, followed by a slow, sustained release of the drug to the target release when the drug is combined with a polymer carrier. In other embodiments the composition does not include an SRF. In these embodiments the composition may consist essentially of one or more drugs and solvent.

According to the disclosure, useful drug or drug combinations used in the composition include a cytostatic drug, cytotoxic drug, and/or other drugs. The other drug(s) may be used by themselves (i.e., the “other drug(s)” are the only active agents in the composition), or in combination with the cytostatic drug or cytotoxic drug as part of the medical procedure for treatment of BPH. For example, the other drug(s) may be administered before the composition is injected into the target tissue using a needle syringe, or the other drug(s) may be included in the composition. Or the other drug(s) may be administered after the composition containing the cytostatic drug or cytotoxic drug is administered to the target tissue.

These other drugs, which may be administered with, or instead of the cytostatic or cytotoxic drug, include alpha blockers or 5-alpha reductase inhibitors. Alpha blockers may include and are not limited to terazosin, doxazosin, tamsulosin, alfuzosin, and silodosin. 5-alpha reductase inhibitors may include and are not limited to finasteride and dutasteride. Anti-inflammatory drugs may include but are not limited to corticosteroids such as dexamethasone, fluticasone propionate, triamcinolone acetonide, mometasone furoate, prednisone, hydrocortisone, estradiol, clobetasol, and budesonide. Non-steroidal drugs may include acetaminophen, ibuprofen, and naproxen. These other drug types may block cytokine activity or inhibit binding of cytokines to inhibit inflammatory signals such as anti-IL1, anti-IL 2, anti-IL3, anti-IL4, anti-IL8, anti-IL15, anti-IL 18, anti-MCP 1, anti-CCR2, anti-GM-CSF, anti-TNF antibodies and others.

Five alpha reductase inhibitors reduce the prostate volume by 50% when given orally. Minimal reduction occurs in less than six months. An up to 50% reduction in prostate volume is expected in 12-24 months or possibly longer with appropriate therapy. Alpha blockers can also be used to treat symptomatically at the time of procedure by blocking the alpha receptor and relaxing the prostate smooth muscle. Alpha blockers, five alpha reductase inhibitors or both may be co-formulated with cytostatic or cytotoxic drugs in the composition.

Solvents

The composition with, or without SRF, is delivered to the target tissue in the form of a composition in liquid form. The composition may be made by dissolving the SRF components in a suitable solvent. Suitable solvents for use in a composition with, or without an SRF, include water, N-methyl pyrrolidone (NMP), dimethyl sulfoxide (DMSO), 2-pyrrolidone, propylene carbonate, caprolactam, triacetin, alcohols, benzyl benzoate, ethyl acetate, triethyl citrate, benzyl alcohol, glyme (dim ethoxyethane), diglyme, and other glycol ethers, and dichloromethane, or any mixture thereof.

Compositions with SRF

Embodiments of compositions including an SRF and intended for direct needle injection into the transition section of the prostate are set forth in TABLE 1.

TABLE 1

Examples of constituents by % vol in a composition with a SRF

| Example | Drug | Polymer | SRF (drug & polymer %) | SRF (solvent %) |
|---|---|---|---|---|
| 1 | Paclitaxel (4.3%) | PLGA 50/50 (47.8%) | 52.1% (polymer + drug) | NMP 47.8% |
| 2 | Sirolimus (4.3%) | PLGA 85/15 (47.8%) | 52.1% (polymer + drug) | NMP 47.8% |
| 3 | Paclitaxel (3.6%) | PLGA 50/50 (48.2%) | 51.8% (polymer + drug) | NMP 48.2% |
| 4 | Sirolimus (3.4%) | PLGA 85/15 (48.3%) | 51.8% (polymer + drug) | NMP 48.3% |
| 5 | Paclitaxel (5.0%) | PLGA 50/50 (47.5%) | 52.5% (polymer + drug) | NMP 47.5% |
| 6 | Sirolimus (5.0%) | PLGA 85/15 (47.5%) | 52.5% (polymer + drug) | NMP 47.5% |
| 7 | Sirolimus (7.0%) | PLGA 50/50 (46.5%) | 53.5% (polymer + drug) | NMP 46.5% |
| 8 | Sirolimus (7.0%) | PLGA 85/15 (46.5%) | 53.5% (polymer + drug) | NMP 46.5% |
| 9 | Paclitaxel (7.0%) | PLGA 50/50 (46.5%) | 53.5% (polymer + drug) | NMP 46.5% |
| 10 | Paclitaxel (7.0%) | PLGA 85/15 (46.5%) | 53.5% (polymer + drug) | NMP 46.5% |
| 11 | Sirolimus (8.0%) | PLGA 50/50 (37.5%) | 45.5% (polymer + drug) | NMP 54.5% |
| 12 | Sirolimus (8.0%) | PLGA 85/15 (37.5%) | 45.5% (polymer + drug) | NMP 54.5% |
| 13 | Paclitaxel (8.0%) | PLGA 50/50 (37.5%) | 45.5% (polymer + drug) | NMP 54.5% |
| 14 | Paclitaxel (8.0%) | PLGA 85/15 (37.5%) | 45.5% (polymer + drug) | NMP 54.5% |
| 15 | Sirolimus (9.0%) | PLGA 50/50 (40.0%) | 49.0% (polymer + drug) | NMP 51.0% |
| 16 | Sirolimus (9.0%) | PLGA 85/15 (40.0%) | 49.0% (polymer + drug) | NMP 51.0% |
| 17 | Paclitaxel (9.0.%) | PLGA 50/50 (40.0%) | 49.0% (polymer + drug) | NMP 51.0% |
| 18 | Paclitaxel (9.0%) | PLGA 85/15 (40.0%) | 49.0% (polymer + drug) | NMP 51.0% |
| 19 | Sirolimus (10.0%) | PLGA 50/50 (40.0%) | 50.0% (polymer + drug) | NMP 50.0% |
| 20 | Sirolimus (10.0%) | PLGA 85/15 (40.0%) | 50.0% (polymer + drug) | NMP 50.0% |
| 21 | Paclitaxel (10.0%) | PLGA 50/50 (40.0%) | 50.0% (polymer + drug) | NMP 50.0% |
| 22 | Paclitaxel (10.0%) | PLGA 85/15 (40.0%) | 50.0% (polymer + drug) | NMP 50.0% |
| 23 | Sirolimus (12.0%) | PLGA 50/50 (35.0%) | 47.0% (polymer + drug) | NMP 53.0% |
| 24 | Sirolimus (12.0%) | PLGA 85/15 (35.0%) | 47.0% (polymer + drug) | NMP 53.0% |
| 25 | Paclitaxel (12.0%) | PLGA 50/50 (35.0%) | 47.0% (polymer + drug) | NMP 53.0% |
| 26 | Paclitaxel (12.0%) | PLGA 85/15 (35.0%) | 47.0% (polymer + drug) | NMP 53.0% |
| 28 | Paclitaxel (16.0%) | PLGA 50/50 (32.0%) | 48.0% (polymer + drug) | NMP 52.0% |
| 29 | Paclitaxel (16.0%) | PLGA 85/15 (32.0%) | 48.0% (polymer + drug) | NMP 52.0% |
| 30 | Paclitaxel (20.0%) | PLGA 50/50 (28.0%) | 48.0% (polymer + drug) | NMP 52.0% |
| 31 | Paclitaxel (20.0%) | PLGA 85/15 (28.0%) | 48.0% (polymer + drug) | NMP 52.0% |

The composition with SRF may have a bioabsorbable polymer at a concentration of 20-80%, 25-75%, 40-60% by wt. of the bioabsorbable polymer composition, 80-20%, 75-25%, 60-40%, by wt. of the solvent and 0.5%-30% by wt. drug; 1%-20% by wt. of drug, or 1%-5% by wt. of drug.

The composition with SRF may comprise 0.1-60% of a polymer composition, or more preferable 30-50% of a polymer composition. The drug to polymer weight ratio of the SRF may be 1:100, 1:50, 1:25, 1:20, 1:10, 1:5, 1:2, 1:1, 2:1, or 5:1. The SRF, once located at the target tissue, may release 1-10%, or 11-50% of the drug load in less than 24 hours, 24-72 hours, 3-7 days, 1-4 weeks, 1-3 months or more than 3 months. The SRF may release 80-100% in 24-72 h, 3-7 days, 1-4 weeks, 1-3 months or more than 3 months.

The composition with SRF may include a polymer composition including silk-elastin like protein polymers, Pluronics F68 or F127 or a combination thereof, poly(ε-caprolactone) (PC), polylactides (PLA), poly(D,L-lactide) (PDLA), poly(ortho esters), polyanhydrides, polycarbonates, polyethylene glycol (PEG), polyethylene oxide (PEO), polyesteramides, and any combinations thereof including block and random co-polymers such as but not limited to poly(lactide-co-glycolide) (PLGA) and PLGA-PEG-PLGA. More specifically the PLGA composition may consist of poly(D,L-lactide-co-glycolide) (50:50), poly(D-lactide-co-glycolide) (50:50), poly(L-lactide-co-glycolide) (50:50), poly(D,L-lactide-co-glycolide) (65:35), poly(D-lactide-co-glycolide) (65:35), poly(L-lactide-co-glycolide) (65:35), poly(D,L-lactide-co-glycolide) (75:25), poly(D-lactide-co-glycolide) (75:25), poly(L-lactide-co-glycolide) (75:25), poly(D,L-lactide-co-glycolide) (85:15) or a mixture thereof. The PLGA may be end-capped with ester, acid, alcohol, thiol or other end-groups. The inherent viscosity of the PLGA polymer may vary from 0.1 dL/g to greater than 1.0 dL/g. The molecular weight of the PLGA polymer may vary from 10 kDa up to 150 kDa. The polymer may be linear, branched, hyperbranched, dendritic, have a star structure, or be a dendrimer-like star polymer.

The composition with SRF may include a polymer composition including poly(lactide-co-glycolide), poly(D,L-lactide-co-glycolide), poly(D,L-lactide), ester end capped poly (D,L-lactide-co-glycolide) (50-50), ester end capped poly (D,L-lactide-co-glycolide) (65-35), ester end capped poly (D,L-lactide-co-glycolide (75-25), ester end capped poly(D, L-lactide-co-glycolide (85-15), acid end capped poly(D,L-lactide-co-glycolide) (50-50), acid end capped poly(D,L-lactide-co-glycolide) (65-35), acid end capped poly(D,L-lactide-co-glycolide (75-25), acid end capped poly(D,L-lactide-co-glycolide (85-15), ester end capped poly(D-lactide-co-glycolide) (50-50), ester end capped poly(D-lactide-co-glycolide) (65-35), ester end capped poly(D-lactide-co-glycolide (75-25), acid end capped poly(D-lactide-co-glycolide) (50-50), acid end capped poly(D-lactide-co-glycolide) (65-35), acid end capped poly(D-lactide-co-glycolide (75-25), ester end capped poly(L-lactide-co-glycolide) (50-50), ester end capped poly(L-lactide-co-glycolide) (65-35), ester end capped poly(L-lactide-co-glycolide (75-25), acid end capped poly(L-lactide-co-glycolide) (50-50), acid end capped poly(L-lactide-co-glycolide) (65-35), acid end capped poly(L-lactide-co-glycolide (75-25), ester end capped poly(D,L-lactide-co-glycolide), acid end capped poly(D,L-lactide-co-glycolide), or combinations thereof.

In some embodiments the composition with SRF may include a bioabsorbable polymer composition and the inherent viscosity of the polymer composition is between 0.05-1.0 dL/g, 0.1-0.6 dL/g, or 0.1 to 0.4 dL/g or 0.1 to 0.3 dL/g and the ratio of DL-lactide to glycolide is from 30/70 up to 90/10, 95/5, or 85/15.

In some embodiments the composition with SRF may include a bioabsorbable polymer at a concentration of 20-80%, 25-75%, 40-60% by wt. of the bioabsorbable polymer composition, 80-20%, 75-25%, 60-40%, by wt. of the solvent and 0.5%-30% by wt. drug; 1%-20% by wt. of drug, or 1%-10% by wt. of drug.

The drug carrier (polymer composition) may generally be in the form of amorphous or semi-crystalline, homogenous, or phase-separated, and provided in the form of a liquid solution or, suspension, or as nanoparticles, microspheres or microparticles processed by spray drying, emulsion, electrospray, or extrusion. The biodegradable polymer composition is preferably chosen to substantially biodegrade in a period of about 1 to 3 months, 3 to 6 months or 6 to 12 months.

Suitable solvents for these embodiments include water, N-methylpyrrolidone (NMP), dimethyl sulfoxide (DMSO), 2-pyrrolidone, propylene carbonate, caprolactam, triacetin, alcohols, benzyl benzoate, ethyl acetate, triethyl citrate, benzyl alcohol, glyme (dimethoxyethane), diglyme, and other glycol ethers, and dichloromethane, or any mixture thereof.

As explained earlier, the composition should be formulated at a concentration and viscosity that permits passage through a long, narrow needle having a slenderness ratio within the prescribed ranges deliverable in low unit volumes, and controls the drug release, and drug distribution. Drug to polymer ratios, which influence the viscosity of the composition, may vary from 0.025 to 2.0. Drug and polymer concentrations in solvent may range from 0.1 wt % up to 60 wt % or more preferably 30 wt % to 50 wt %. Total volume of the composition for a treatment may range from 0.050 mL up to 1.5 mL or more preferably 0.10 mL to 1.0 mL. Overall dosage of drug provided in the SRF can range from 50 ug up to 200 mg or more preferably from 5 mg to 50 mg. For example, a composition containing the SRF is 300 ug of sirolimus or paclitaxel dissolved with 3000 ug ("ug"—micrograms) poly (D, L-lactide-co-glycolide) (85:15) in NMP at a 50 wt % concentration.

Composition without SRF

Embodiments of compositions without an SRF and intended for direct needle injection into the transition section of the prostate are set forth in TABLE 2.

TABLE 2

Examples of constituents by % vol in a composition without a SRF

| Example | Drug | Solvent |
|---|---|---|
| 1 | 5% | 95% |
| 2 | 10% | 90% |
| 3 | 15% | 85% |
| 4 | 20% | 80% |
| 5 | 25% | 75% |
| 6 | 30% | 70% |
| 7 | 35% | 65% |
| 8 | 40% | 60% |
| 9 | 45% | 55% |
| 10 | 50% | 50% |
| 11 | 55% | 45% |
| 12 | 60% | 40% |

It will be appreciated that the % by volume content of the drug is very high for direct needle injection into the prostate. According to some embodiments, small unit volume sizes, such as from 2 microliters to 25 microliters, 5-10 microliters or 10-25 microliters, may be selected for compositions that do not include an SRF, or fewer implants are placed in the prostate when there is a higher drug concentration in the composition. In certain embodiments, the treatment does not go over 100 mg of drug for any size prostate.

The implant size may be selected to arrive at the best balance between volume size and accuracy of dose dispensed. A small implant size reduces pressure on the urethra when implanted but may also reduce accuracy of the exact volume of drug dispensed if the implant size is very small. In certain embodiments a dose dispensing device with high accuracy is used with the needle syringe, e.g., the device described in connection with FIG. 6.

In certain embodiments, the composition is selected from the embodiments below.

In one embodiment, 0.5 mL N-methyl pyrrolidone (NMP) was added to a vial with 0.25 g sirolimus and vortexed until dissolved. 50 microliter of drug solution was added to 2.5 mL of a 50% PLGA8515A (0.3 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 50 microliter of drug solution was added to 2.5 mL of a 50% PLGA8515A (0.5 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 50 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 50 microliter of drug solution was added to 2.5 mL of a 50% PLGA8515E (0.5 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 50 microliter of drug solution was added to 2.5 mL of a 50% PLGA8515A (0.7 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 50 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 100 microliter of drug solution was added to 2.5 mL of a 50% PLGA8515A (0.3 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 100 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 100 microliter of drug solution was added to 2.5 mL of a 50% PLGA8515A (0.5 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 100 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 100 microliter of drug solution was added to 2.5 mL of a 50% PLGA8515E (0.3 dl/g) in NMP solution using syringe to syringe mixing with a female to female luer connector. 500 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 100 microliter of drug solution was added to 2.5 mL of a 50% PLGA8515A (0.5 dl/g) in NMP solution using syringe to syringe mixing with a female to female luer connector. 500 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 100 microliter of drug solution was added to 2.5 mL of a 50% PLGA8515E (0.7 dl/g) in NMP solution using syringe to syringe mixing with a female to female luer connector. 500 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 200 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 50 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 100 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 200 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers In another embodiment, 0.5 mL N-methyl pyrrolidone (NMP) was added to a vial with 0.25 g sirolimus and vortexed until dissolved. 50 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 100 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g sirolimus and vortexed until dissolved. 200 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 50 microliter of drug solution was added to 2.5 mL of a 50% PLGA8515A (0.3 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 50 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 50 microliter of drug solution was added to 2.5 mL of a 50% PLGA8515A (0.5 dl/g) in NMP solution using syringe to syringe mixing with a female to female luer connector. 250 microliters in a 1 mL syringe was loaded into a 20 G×20 cm Chiba biopsy needle with depth markers. 0.5 mL N-methyl pyrrolidone (NMP) was added to a vial with 0.25 g everolimus and vortexed until dissolved. 50 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 50 microliter of drug solution was added to 2.5 mL of a 50% PLGA8515A (0.5 dl/g) in NMP solution using syringe to syringe mixing with a female to female luer connector. 500 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 50 microliter of drug solution was added to 2.5 mL of a 50% PLGA8515E (0.7 dl/g) in NMP solution using syringe to syringe mixing with a female to female luer connector. 500 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 50 microliter of drug solution was added to 2.5 mL of a 50% PLGA8515E (0.5 dl/g) in NMP solution using syringe to syringe mixing with a female to female luer connector. 800 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 50 microliter of drug solution was added to 2.5 mL of a 50% PLGA8515A (0.7 dl/g) in NMP solution using syringe to syringe mixing with a female to female luer connector. 800 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 50 microliter of drug solution was added to 2.5 mL of a 50% PLGA8515A (0.7 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 50 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 100 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 200 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 50 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 100 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 200 microliter of drug solution was added to 2.5 mL of a 50% PLGA7525A (0.3 dl/g) in NMP solution using syringe to syringe mixing with a female to female luer connector. 250 microliters in a 1 mL syringe was loaded into a 20 G×20 cm Chiba biopsy needle with depth markers In another embodiment, 0.5 mL N-methyl pyrrolidone (NMP) was added to a vial with 0.25 g everolimus and vortexed until dissolved. 200 microliter of drug solution was added to 2.5 mL of a 50% PLGA7525E (0.3 dl/g) in NMP solution using syringe to syringe mixing with a female to female luer connector. 250 microliters in a 1 mL syringe was loaded into a 20 G×20 cm Chiba biopsy needle with depth markers In another embodiment, 0.5 mL N-methyl pyrrolidone (NMP) was added to a vial with 0.25 g everolimus and vortexed until dissolved. 200 microliter of drug solution was added to 2.5 mL of a 50% PLGA7525A (0.5 dl/g) in NMP solution using syringe to syringe mixing with a female to female luer connector. 250 microliters in a 1 mL syringe was loaded into a 20 G×20 cm Chiba biopsy needle with depth markers In another embodiment, 0.5 mL N-methyl pyrrolidone (NMP) was added to a vial with 0.25 g everolimus and vortexed until dissolved. 200 microliter of drug solution was added to 2.5 mL of a 50% PLGA7525E (0.5 dl/g) in NMP solution using syringe to syringe mixing with a female to female luer connector. 250 microliters in a 1 mL syringe was loaded into a 20 G×20 cm Chiba biopsy needle with depth markers In another embodiment, 0.5 mL N-methyl pyrrolidone (NMP) was added to a vial with 0.25 g everolimus and vortexed until dissolved. 200 microliter of drug solution was added to 2.5 mL of a 50% PLGA7525A (0.7 dl/g) in NMP solution using syringe to syringe mixing with a female to female luer connector. 250 microliters in a 1 mL syringe was loaded into a 20 G×20 cm Chiba biopsy needle with depth markers In another embodiment, 0.5 mL N-methyl pyrrolidone (NMP) was added to a vial with 0.25 g everolimus and vortexed until dissolved. 200 microliter of drug solution was added to 2.5 mL of a 50% PLGA7525E (0.7 dl/g) in NMP solution using syringe to syringe mixing with a female to female luer connector. 250 microliters in a 1 mL syringe was loaded into a 20 G×20 cm Chiba biopsy needle with depth markers In another embodiment, 0.5 mL N-methyl pyrrolidone (NMP) was added to a vial with 0.25 g everolimus and vortexed until dissolved. 200 microliter of drug solution was added to 2.5 mL of a 50% PLGA6535E (0.3 dl/g) in NMP solution using syringe to syringe mixing with a female to female luer connector. 250 microliters in a 1 mL syringe was loaded into a 20 G×20 cm Chiba biopsy needle with depth markers In another embodiment, 0.5 mL N-methyl pyrrolidone (NMP) was added to a vial with 0.25 g everolimus and vortexed until dissolved. 200 microliter of drug solution was added to 2.5 mL of a 50% PLGA6535A (0.3 dl/g) in NMP solution using syringe to syringe mixing with a female to female luer connector. 250 microliters in a 1 mL syringe was loaded into a 20 G×20 cm Chiba biopsy needle with depth markers In another embodiment, 0.5 mL N-methyl pyrrolidone (NMP) was added to a vial with 0.25 g everolimus and vortexed until dissolved. 200 microliter of drug solution was added to 2.5 mL of a 50% PLGA6535E (0.5 dl/g) in NMP solution using syringe to syringe mixing with a female to female luer connector. 250 microliters in a 1 mL syringe was loaded into a 20 G×20 cm Chiba biopsy needle with depth markers In another embodiment, 0.5 mL N-methyl pyrrolidone (NMP) was added to a vial with 0.25 g everolimus and vortexed until dissolved. 200 microliter of drug solution was added to 2.5 mL of a 50% PLGA6535A (0.5 dl/g) in NMP solution using syringe to syringe mixing with a female to female luer connector. 250 microliters in a 1 mL syringe was loaded into a 20 G×20 cm Chiba biopsy needle with depth markers In another embodiment, 0.5 mL N-methyl pyrrolidone (NMP) was added to a vial with 0.25 g everolimus and vortexed until dissolved. 200 microliter of drug solution was added to 2.5 mL of a 50% PLGA6535E (0.5 dl/g) in NMP solution using syringe to syringe mixing with a female to female luer connector. 500 microliters in a 1 mL syringe was loaded into a 20 G×20 cm Chiba biopsy needle with depth markers In another embodiment, 0.5 mL N-methyl pyrrolidone (NMP) was added to a vial with 0.25 g everolimus and vortexed until dissolved. 200 microliter of drug solution was added to 2.5 mL of a 50% PLGA6535A (0.5 dl/g) in NMP solution using syringe to syringe mixing with a female to female luer connector. 500 microliters in a 1 mL syringe was loaded into a 20 G×20 cm Chiba biopsy needle with depth markers In another embodiment, 0.5 mL N-methyl pyrrolidone (NMP) was added to a vial with 0.25 g everolimus and vortexed until dissolved. 50 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 100 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g everolimus and vortexed until dissolved. 200 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 50 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 100 microliter of drug solution was added to 2.5 mL of a 50% PLGA8515A (0.3 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 100 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 100 microliter of drug solution was added to 2.5 mL of a 50% PLGA8515A (0.5 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 100 microliter of drug solution was added to 2.5 mL of a 50% PLGA8515E (0.5 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 100 microliter of drug solution was added to 2.5 mL of a 50% PLGA8515A (0.7 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 100 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 100 microliter of drug solution was added to 2.5 mL of a 50% PLGA8515A (0.5 dl/g) in NMP solution using syringe to syringe mixing with a female to female luer connector. 500 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 100 microliter of drug solution was added to 2.5 mL of a 50% PLGA8515E (0.5 dl/g) in NMP solution using syringe to syringe mixing with a female to female luer connector. 500 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 100 microliter of drug solution was added to 2.5 mL of a 50% PLGA8515A (0.7 dl/g) in NMP solution using syringe to syringe mixing with a female to female luer connector. 500 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 500 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 200 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 50 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 100 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 200 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers In another embodiment, 0.5 mL N-methyl pyrrolidone (NMP) was added to a vial with 0.25 g paclitaxel and vortexed until dissolved. 100 microliter of drug solution was added to 2.5 mL of a 50% PLGA6535A (0.3 dl/g) in NMP solution using syringe to syringe mixing with a female to female luer connector. 500 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 100 microliter of drug solution was added to 2.5 mL of a 50% PLGA6535A (0.5 dl/g) in NMP solution using syringe to syringe mixing with a female to female luer connector. 500 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 500 microliter of drug solution was added to 2.5 mL of a 50% PLGA6535E (0.3 dl/g) in NMP solution using syringe to syringe mixing with a female to female luer connector. 250 microliters in a 1 mL syringe was loaded into a 20 G×20 cm Chiba biopsy needle with depth markers.

In another embodiment, 0.5 mL N-methyl pyrrolidone (NMP) was added to a vial with 0.25 g paclitaxel and vortexed until dissolved. 500 microliter of drug solution was added to 2.5 mL of a 50% PLGA6535E (0.5 dl/g) in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.25 g paclitaxel and vortexed until dissolved. 400 mg of drug solution was added to 2.9 g of a 20% by weight PLGA5050A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 30% by weight PLGA5050A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 40% by weight PLGA5050A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 40% by weight PLGA5050A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 50% by weight PLGA5050A in NMP solution using syringe to syringe mixing with a female to female luer connector (#SRF1A). 250 microliters in a 1 mL syringe was loaded into a 20 G×20 cm Chiba biopsy needle with depth markers.

In another embodiment, 1.08 g N-methyl pyrrolidone (NMP) was added to a vial with 0.90 g paclitaxel and vortexed until dissolved. 591 mg of drug solution was added to 2.9 g of a 50% by weight PLGA5050A in NMP solution using syringe to syringe mixing with a female to female luer connector (#SRF1B). 250 microliters in a 1 mL syringe was loaded into a 20 G×20 cm Chiba biopsy needle with depth markers.

In another embodiment, 1.08 g N-methyl pyrrolidone (NMP) was added to a vial with 0.90 g paclitaxel and vortexed until dissolved. 391 mg of drug solution was added to 2.9 g of a 50% by weight PLGA5050A in NMP solution using syringe to syringe mixing with a female to female luer connector (#SRF1C). 250 microliters in a 1 mL syringe was loaded into a 20 G×20 cm Chiba biopsy needle with depth markers.

In another embodiment, 1.08 g N-methyl pyrrolidone (NMP) was added to a vial with 0.90 g paclitaxel and vortexed until dissolved. 791 mg of drug solution was added to 2.9 g of a 50% by weight PLGA5050A in NMP solution using syringe to syringe mixing with a female to female luer connector (#SRF1D). 250 microliters in a 1 mL syringe was loaded into a 20 G×20 cm Chiba biopsy needle with depth markers.

In another embodiment, 1.08 g N-methyl pyrrolidone (NMP) was added to a vial with 0.90 g paclitaxel and vortexed until dissolved. 591 mg of drug solution was added to 2.9 g of a 50% by weight PLGA6535A in NMP solution using syringe to syringe mixing with a female to female luer connector (#SRF1E). 250 microliters in a 1 mL syringe was loaded into a 20 G×20 cm Chiba biopsy needle with depth markers.

In another embodiment, 1.08 g N-methyl pyrrolidone (NMP) was added to a vial with 0.90 g paclitaxel and vortexed until dissolved. 391 mg of drug solution was added to 2.9 g of a 50% by weight PLGA6535A in NMP solution using syringe to syringe mixing with a female to female luer connector (#SRF1F). 250 microliters in a 1 mL syringe was loaded into a 20 G×20 cm Chiba biopsy needle with depth markers.

In another embodiment, 1.08 g N-methyl pyrrolidone (NMP) was added to a vial with 0.90 g paclitaxel and vortexed until dissolved. 791 mg of drug solution was added to 2.9 g of a 50% by weight PLGA6535A in NMP solution using syringe to syringe mixing with a female to female luer connector (#SRF1G). 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 50% by weight PLGA5050A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.25 g paclitaxel and vortexed until dissolved. 400 mg of drug solution was added to 2.9 g of a 20% by weight PLGA5050E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 30% by weight PLGA5050E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 40% by weight PLGA5050E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 40% by weight PLGA5050E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 50% by weight PLGA5050E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 50% by weight PLGA5050E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.25 g paclitaxel and vortexed until dissolved. 400 mg of drug solution was added to 2.9 g of a 20% by weight PLGA8515A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 30% by weight PLGA8515A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 40% by weight PLGA8515A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 40% by weight PLGA8515A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 50% by weight PLGA8515A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 50% by weight PLGA8515A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.25 g paclitaxel and vortexed until dissolved. 400 mg of drug solution was added to 2.9 g of a 20% by weight PLGA8515E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 30% by weight PLGA8515E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 40% by weight PLGA8515E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 40% by weight PLGA8515E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 50% by weight PLGA8515E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 50% by weight PLGA8515E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.25 g paclitaxel and vortexed until dissolved. 400 mg of drug solution was added to 2.9 g of a 20% by weight PLGA6535A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 30% by weight PLGA6535A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 40% by weight PLGA6535A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 40% by weight PLGA6535A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 50% by weight PLGA5050A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 50% by weight PLGA6535A in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.25 g paclitaxel and vortexed until dissolved. 400 mg of drug solution was added to 2.9 g of a 20% by weight PLGA6535E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 30% by weight PLGA6535E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 40% by weight PLGA6535E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 40% by weight PLGA6535E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 50% by weight PLGA6535E in NMP solution using syringe to syringe mixing with a female to female luer connector. 250 microliters in a 1 mL syringe was loaded into a 20 G×20 cm Chiba biopsy needle with depth markers.

In another embodiment, 1.08 g N-methyl pyrrolidone (NMP) was added to a vial with 0.50 g paclitaxel and vortexed until dissolved. 400 mg of drug solution was added to 2.9 g of a 50% by weight PLGA6535E in NMP solution using syringe to syringe mixing with a female to female luer connector. 250 microliters in a 1 mL syringe was loaded into a 20 G×20 cm Chiba biopsy needle with depth markers.

Examples

An in-human study was conducted of IntraProstatic Drug Eluting (IPDE) bioabsorbable implants for treatment of Lower Urinary Tract Symptoms (LUTS) secondary to Benign Prostatic Hyperplasia (BPH).

Figure 5A:
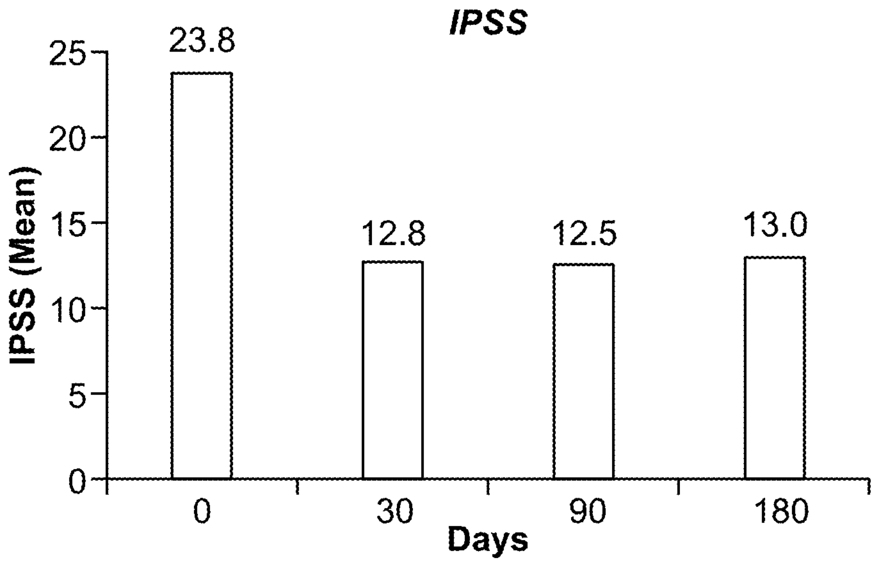
FIG. 5A is bar chart showing mean International Prostate Symptom Scores (IPSS) from an human study of Benign Prostatic Hyperplasia (BPH) patients treated with IntraProstatic Drug Eluting (IPDE) bioabsorbable implants according to the one or more of the systems and methods of treatment disclosed herein. Results shown are for IPSS scores taken prior to treatment, and 30, 90 and 180 days from treatment.
Figure 5B:
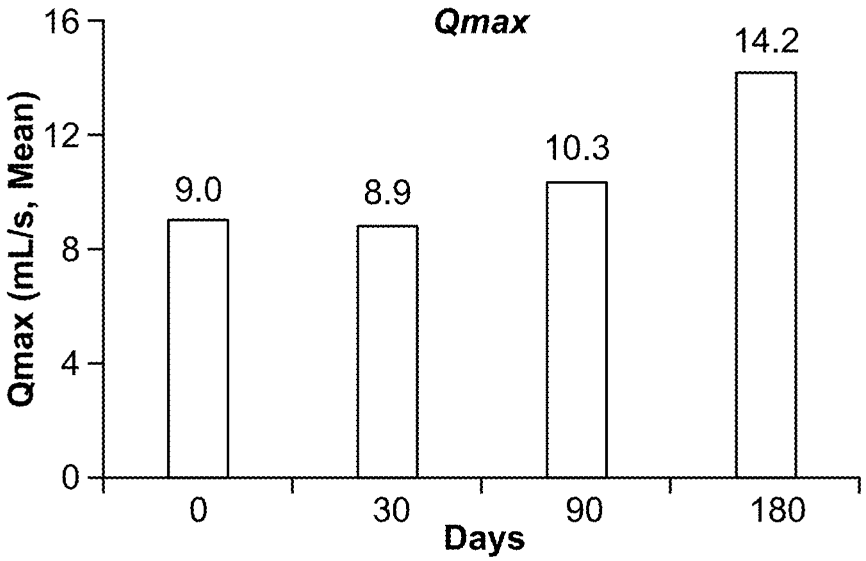
FIG. 5B shows mean Qmax rates from an human study of Benign Prostatic Hyperplasia (BPH) patients treated with IntraProstatic Drug Eluting (IPDE) bioabsorbable implants according to one or more of the systems and methods of treatment disclosed herein. Results shown are for IPSS scores taken prior to treatment, and 30, 90 and 180 days from treatment.

The results from this study are shown in FIGS. 5A, 5B. The Intraprostatic Drug Elution (IPDE) therapy used paclitaxel eluting bioabsorbable implants to treat men suffering from lower urinary tract symptoms (LUTS) secondary to benign prostatic hyperplasia (BPH).

Figure 4:
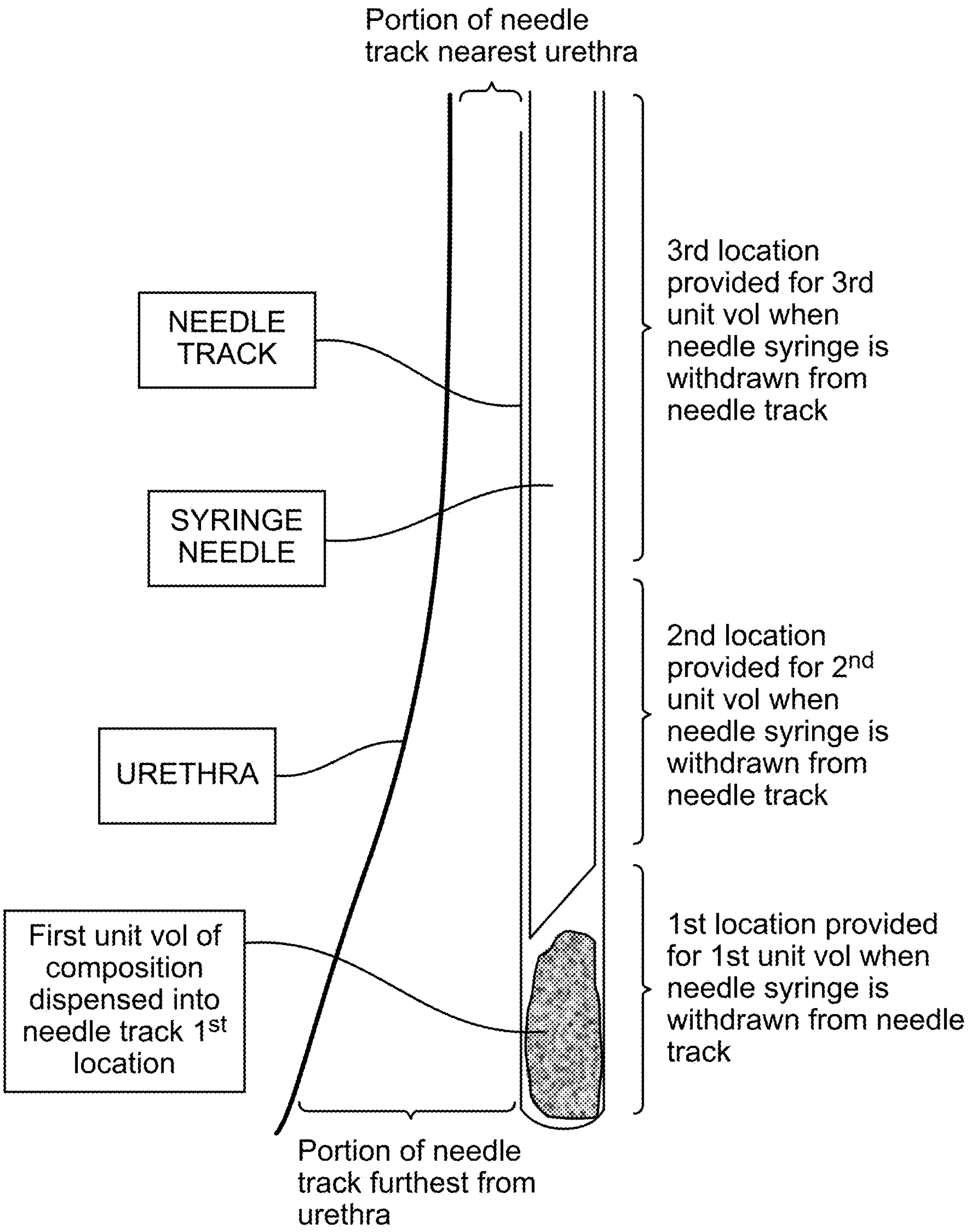
FIG. 4 is annotated cross-sectional depiction showing an urethra length portion and position of needle and needle track relative to the urethra length portion. It shows a first, second and third location within the same needle track. The first location was made available for the unit volume when the needle was withdrawn from the needle track. The needle is later further withdrawn from the needle track a second and third time to make, respectively, second and third portions for an implant.

FIG. 4 is an image capture from an ultrasound device (TRUS device) used to capture sagittal and transverse views of the prostate. The view shown was taken for a patient being treated by transperineal access to the prostate under the study.

4-24 implants of the IPDE therapy were delivered by transperineal implantation guided by transrectal ultrasound imaging using a 20 gauge syringe needle. The key eligibility inclusion criteria for the study included age ≥50 years, international prostate symptom score (IPSS) ≥13, peak urine flow rate ≥5 mL/sec and ≤15 mL/sec, voided volume ≥100 mL, post-void residual urine volume ≤250 mL, prostate volume between 25 to 100 cc (or 25 to 100 g), and inadequate response and/or refusal of medical therapy for LUTS.

Initial IPDE dosing of 5 patients (mean age of 63 years) was performed, each patient received 4-6 paclitaxel eluting bioabsorbable implants at a lower dose cohort.

Visual analogue scale (VAS) pain levels at procedure/discharge were 0.0 with no post procedure catheterization. Mean follow-up VAS pain levels were 1.2 at 1 day and 0.0 at 7 days post treatment.

IPSS decreased by 11 points from baseline 90 days after treatment with 75% of patients showing improvement of symptoms. Qmax increased by 5 mL/s from baseline per protocol 180 days after treatment.

No serious drug or procedure related adverse events have been reported to date. Anticipated observations reported such as minor bleeding/bruising and pain/discomfort were all mild and resolved within 7 days or less from treatment.

FIG. 5A is bar chart showing mean International Prostate Symptom Scores (IPSSs) from the in-human study of Benign Prostatic Hyperplasia (BPH) patients treated with IntraProstatic Drug Eluting (IPDE) bioabsorbable implants according to the disclosure. Results shown are for IPSS scores taken prior to treatment, and 30, 90 and 180 days from treatment. The mean IPSS score decreased from 23.8 points to 13 points from baseline to 180 days after treatment, indicating a significant improvement in BPH symptoms.

FIG. 5B shows mean Qmax rates from the in-human study of Benign Prostatic Hyperplasia (BPH) patients treated with IntraProstatic Drug Eluting (IPDE) bioabsorbable implants according to the disclosure. Results shown are for IPSS scores taken prior to treatment, and 30, 90 and 180 days from treatment. The mean Qmax rate increased from 9 mL/s to 14.2 mL/s from baseline to 180 days after treatment, indicating a significant improvement in flow rate.

The implant is administered by direct injection (implantation) into the obstructed prostate transition zone under transrectal ultrasound imaging via transperineal (or transrectal) injections/implantations.

Figure 3A:
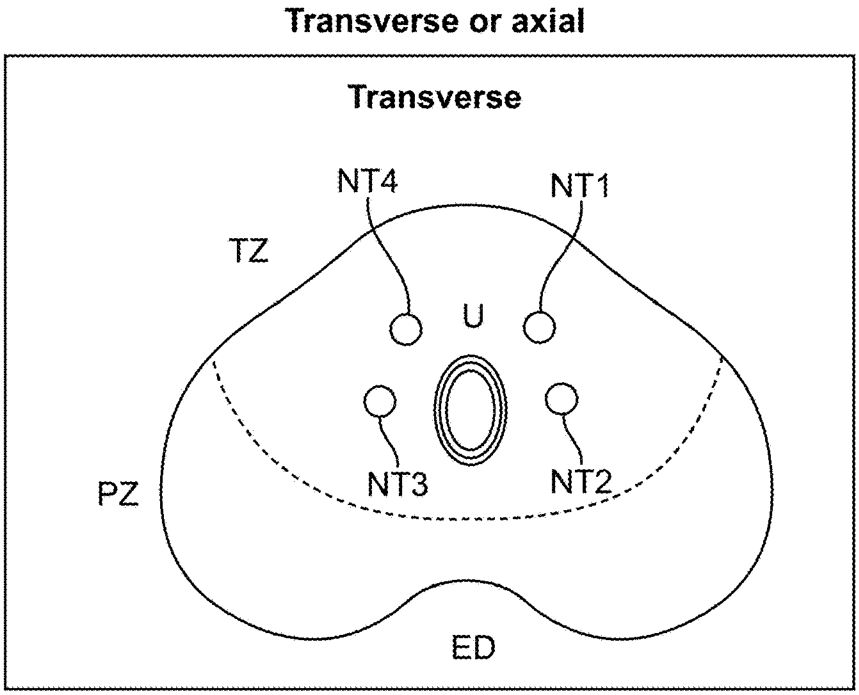
FIG. 3A is a transverse or axial view of a subject's prostate showing a urethra (U) location, transition zone (TZ), peripheral zone (PZ) and locations of four needle tracks (NTs) for dispensing a composition in the prostate. The NT locations NT1, NT2, NT3, and NT4 are approximately located at, respectively, 1, 3, 9 and 11 O'clock positions relative to U.
Figure 3B:
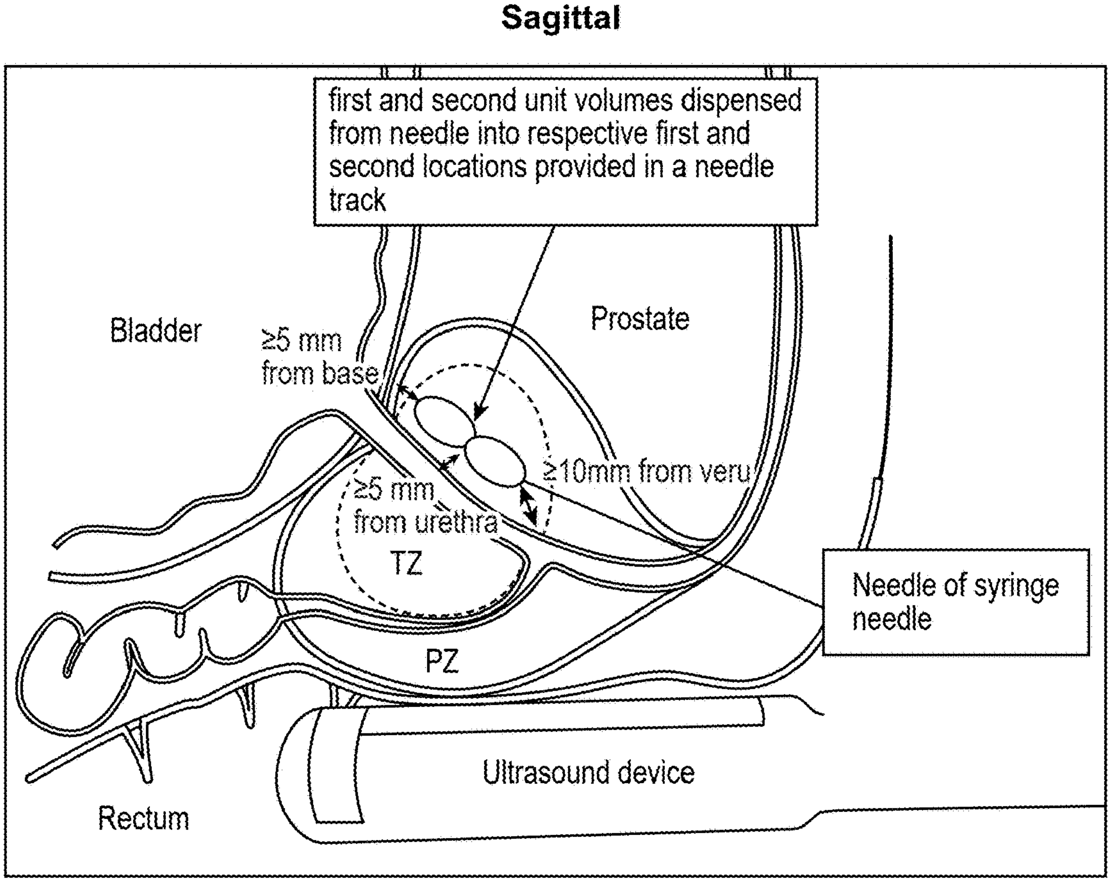
FIG. 3B is a sagittal view of the subject's prostate treatment via transperineal access to prostate. It shows urethra, needle within a needle track made by the needle, first and second implants in the needle track, location of the needle track relative to the urethra, peripheral zone (PZ) near seminal vesicles, Transrectal Ultrasound (TRUS) device and target for BPH transition zone (TZ). This view shows implantation via transperineal implant. Alternatively, prostate treatment may be accomplished by transrectal delivery of the needle, controlled by the TRUS and targeting the same location in the prostate. Additionally shown in FIG. 3B are lengths from implant to bladder neck, implant to verumontanum, and implant to prostate apex.

Implants should be administered to the prostate transition zone along the urethra, between the prostate base, or bladder neck, and the verumontanum (veru). Referring to FIGS. 3B and 4, there is shown the approximate locations for dispensing the implants within the transition zone and needle track providing locations for dispensing the unit volume implants, respectively. The dispensing of the implants, according to some embodiments, should not be closer than 5 mm from the base (or apex) of the prostate to avoid harm to the bladder neck, nor closer than 5 mm from the urethra to avoid damage thereto, nor closer than 10 mm from the veru to avoid harming the seminal vesicle. In some embodiments the implant should also not be further than 10 or 15 mm from the urethra. It is believed than when using a cytotoxic or cytostatic drug according the embodiments, the implant should be no further than 10 or 15 mm nor closer than 3-5 mm from the urethra for a 50 uL or 25 μL unit volume and drug % wt of between 5 and 20% to avoid adverse systematic effects when treating the transition zone, while relieving pressure on the urethra.

Referring to FIG. 4, as can be appreciated, the unit volume is being dispensed into distinct locations of the prostate provided by progressively withdrawing the needle as each unit volume is dispensed. FIG. 4 shows three distinct locations for dispensing the unit volume within the prostate. After withdrawing the needle to provide the first location, the health pro begins the dispensing of the unit volume into the first location. The health waits a period of time to ensure the entire unit volume is dispensed, before withdrawing the needle again to make the second location. This wait time may vary depending on the viscosity of the composition and/or the gauge of the needle used (higher gauge needles may require a longer wait time). For example, when using an 18 gauge needle the wait time may be between 0 and 0.5 seconds, 0.5 seconds and 3 seconds, or up to 5 seconds. For a 20 or 25 gauge needle the wait time may be from 2 to 3 seconds, 1 to 5 seconds, 5 seconds to 10 seconds, or up to 30 seconds. In other embodiments needle gauges of 18-26 G, 19-21 G, 19-20 G may be used.

Prostate volume and implant target locations may be confirmed by transrectal ultrasound imaging via biplanar probe in both the axial and sagittal planes. Images and videos are captured and saved for baseline prostate measurement and treatments of prostate (width, height, length) to determine prostate volume (PV), prostate urethra length (PUL), transition zone volume and urethral length (TZUL) including verumontanum position if possible.

For transperineal implantation under biplanar TRUS guidance: Participant is positioned in the modified lithotomy bed with moveable stirrups; Anesthesia is then applied via transperineal lidocaine block per local protocol or general per site protocol.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

One or more features from any embodiments described herein or in the figures may be combined with one or more features of any other embodiments described herein or in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating Benign Prostatic Hyperplasia (BPH) in a subject in need thereof, comprising:

a) penetrating the subject's prostate with a needle syringe to form a first needle track, b) withdrawing the needle syringe from the first needle track to provide a first location in the needle track for dispensing a composition, c) dispensing no more than a first unit volume of the composition into the first location, d) penetrating the prostate with a needle syringe to form a second needle track spaced from, and on an opposite side of the subject's urethra from the first needle track, e) withdrawing the needle syringe from the second needle track to provide a second location in the second needle track for dispensing the composition, and f) dispensing no more than a second unit volume of the composition into the second location;

wherein the composition comprises an effective amount of docetaxel or paclitaxel and a water-soluble solvent capable of dissolving the docetaxel or paclitaxel into the subject's prostate.

2. A method for treating Benign Prostatic Hyperplasia (BPH) in a subject in need thereof, comprising:

a) penetrating the subject's prostate with a needle syringe to form a first needle track, b) withdrawing the needle syringe from the first needle track to provide a first location in the needle track for dispensing a composition, c) dispensing no more than a first unit volume of the composition into the first location, d) penetrating the prostate with a needle syringe to form a second needle track spaced from, and on an opposite side of the subject's urethra from the first needle track, e) withdrawing the needle syringe from the second needle track to provide a second location in the second needle track for dispensing the composition, and f) dispensing no more than a second unit volume of the composition into the second location;

wherein the composition comprises an effective amount of a cytotoxic or cytostatic drug and a water-soluble solvent capable of dissolving the drug into the subject's prostate; and wherein no portion of the first or second needle track is located nearer than 3-5 mm from the subject's urethra.

3. A method for treating Benign Prostatic Hyperplasia (BPH) in a subject in need thereof, comprising:

a) penetrating the subject's prostate with a needle syringe to form a first needle track, b) withdrawing the needle syringe from the first needle track to provide a first location in the needle track for dispensing a composition, c) dispensing no more than a first unit volume of the composition into the first location, d) penetrating the prostate with a needle syringe to form a second needle track spaced from, and on an opposite side of the subject's urethra from the first needle track, e) withdrawing the needle syringe from the second needle track to provide a second location in the second needle track for dispensing the composition, and f) dispensing no more than a second unit volume of the composition into the second location;

wherein the composition comprises an effective amount of a cytotoxic or cytostatic drug and a water-soluble solvent capable of dissolving the drug into the subject's prostate; and wherein the first location is located on an anterior side of the subject's prostate and/or at least partially contained within a prostate transition zone.

4. The method of claim 1, wherein a plurality of unit volumes of the composition comprising the first unit volume are dispensed into a respective plurality of locations comprising the first location in the first needle track.

5. A method for treating Benign Prostatic Hyperplasia (BPH) in a subject in need thereof, comprising:

a) penetrating the subject's prostate with a needle syringe to form a first needle track, b) withdrawing the needle syringe from the first needle track to provide a first location in the needle track for dispensing a composition, c) dispensing no more than a first unit volume of the composition into the first location, d) penetrating the prostate with a needle syringe to form a second needle track spaced from, and on an opposite side of the subject's urethra from the first needle track, e) withdrawing the needle syringe from the second needle track to provide a second location in the second needle track for dispensing the composition, and f) dispensing no more than a second unit volume of the composition into the second location;

wherein the composition comprises an effective amount of a cytotoxic or cytostatic drug and a water-soluble solvent capable of dissolving the drug into the subject's prostate; and wherein the plurality of unit volumes is dispensed by the following steps performed in the following order:

g) partially withdrawing the needle from the first needle track to provide a second of the plurality of locations in the needle track for dispensing the composition after the first unit volume is dispensed into the first location, and dispensing no more than a second of the plurality of unit volumes into the second of the plurality of locations, and h) partially withdrawing the needle from the first needle track to provide a third of the plurality of locations in the needle track for dispensing the composition after the second of the plurality of unit volumes is dispensed into the second of the plurality of locations, and dispensing no more than a third of the plurality of unit volumes into the third of the plurality of locations.

6. The method of claim 5, wherein the first of the plurality of unit volumes, second of the plurality of unit volumes, and third of the plurality of unit volumes have the same volume or different volumes.

7. The method of claim 3, further comprising the following steps performed in the following order:

g) penetrating the prostate with a needle syringe to form a third needle track, h) withdrawing the needle from the third needle track to provide a third location in the third needle track for dispensing the composition, and i) dispensing no more than a third unit volume of the composition into the third location.

8. The method of claim 1, further comprising the following steps performed in the following order:

j) penetrating the prostate with a needle syringe to form a fourth needle track, k) withdrawing the needle syringe from the fourth needle track to provide a fourth location in the fourth needle track for dispensing the composition, and l) dispensing no more than a fourth unit volume of the composition into the fourth location.

9. A method for treating Benign Prostatic Hyperplasia (BPH) in a subject in need thereof, comprising the following steps in the following order:

forming a needle track in the subject's prostate with a needle syringe, withdrawing the needle syringe from the needle track to provide a first location in the needle track, dispensing a first unit volume of a composition into the first location, withdrawing the needle syringe from the needle track to provide a second location in the needle track, and dispensing a second unit volume of the composition into the second location;

wherein the composition comprises an effective amount of a cytotoxic or cytostatic drug and a water-soluble solvent capable of dissolving the drug in the subject's prostate;

wherein from 1 to 10 dispensed volumes comprising the first unit volume and the second unit volume are dispensed into 1 to 10 locations comprising the first location and the second location; and wherein most, or all of the 1 to 10 dispensed volumes are located no further than 10-15 mm from the subject's urethra.

10. The method of claim 9, wherein the needle syringe is not partially withdrawn to make the second location until after the first unit volume is completely dispensed into the first location.

11. A method for treating Benign Prostatic Hyperplasia (BPH) in a subject in need thereof, comprising the following steps in the following order:

forming a needle track in the subject's prostate with a needle syringe, withdrawing the needle syringe from the needle track to provide a first location in the needle track, dispensing a first unit volume of a composition into the first location, withdrawing the needle syringe from the needle track to provide a second location in the needle track, and dispensing a second unit volume of the composition into the second location;

wherein the composition comprises an effective amount of a cytotoxic or cytostatic drug and a water-soluble solvent capable of dissolving the drug in the subject's prostate; and wherein the needle syringe is partially withdrawn to make the second location not sooner than 0.5 seconds to 30 seconds after the first unit volume is dispensed into the first location.

12. The method of claim 11, wherein a dose delivery device (DDD) dispenses the first unit volume, the DDD including a needle syringe having a needle and an actuator that when actuated causes the DDD to dispense no more than the first unit volume from the needle, wherein the needle is an 18 gauge needle and the 18 gauge needle is not withdrawn until at least from 0.5 sec to 3-10 seconds after the actuator is actuated, or wherein the needle is a 20 gauge needle and the 20 gauge needle is not withdrawn until at least from 1-3 seconds to 30 seconds after the actuator is actuated.

13. A method for treating Benign Prostatic Hyperplasia (BPH) in a subject in need thereof, comprising the steps of:

forming a needle track in the subject's prostate using a needle syringe, withdrawing the needle syringe, and dispensing at least one unit volume of a composition into a first location of the needle track, wherein the dispensing the at least one unit volume into the location is completed at least 15 mm from the prostate apex, and/or wherein the dispensing the at least one unit volume into the location is completed at least 10 mm from the verumontanum;

wherein the composition comprises an effective amount of a cytotoxic or cytostatic drug and a water soluble solvent capable of dissolving the drug into a prostate transition zone.

14. The method of claim 8, wherein the first, second, third, and/or fourth needle tracks are formed with the same needle; or wherein a different needle is used for each of the first, second, third, and/or fourth needle tracks.

15. The method of claim 1, wherein the second unit volume is dispensed into the second location over a period of from 0.5 seconds to 30 seconds after the first unit volume is dispensed into the first location.

16. A method for treating Benign Prostatic Hyperplasia (BPH) in a subject in need thereof, comprising:

a) penetrating the subject's prostate with a needle syringe to form a first needle track, b) withdrawing the needle syringe from the first needle track to provide a first location in the needle track for dispensing a composition, c) dispensing no more than a first unit volume of the composition into the first location, d) penetrating the prostate with a needle syringe to form a second needle track spaced from, and on an opposite side of the subject's urethra from the first needle track, e) withdrawing the needle syringe from the second needle track to provide a second location in the second needle track for dispensing the composition, and f) dispensing no more than a second unit volume of the composition into the second location;

wherein the composition comprises an effective amount of a cytotoxic or cytostatic drug and a water-soluble solvent capable of dissolving the drug into the subject's prostate; and wherein the composition consists essentially of a bioabsorbable polymer, the cytotoxic or cytostatic drug and the solvent.

17. The method of claim 16, wherein the composition has between 5% and 20% vol. of the cytotoxic or cytostatic drug.

18. The method of claim 17, wherein the cytotoxic drug is docetaxel or paclitaxel.

19. The method of claim 1, wherein the unit volume is between 5 μl and 10 μl, 10 μl and 25 μl, 25 μl and 50 μl, or 50 μl and 100 μl.

20. The method of claim 3, wherein the first unit volume and the second unit volume are each independently between 5 μl and 50 μl and the drug is paclitaxel.

* * * * *